US008785187B2

(12) United States Patent
Conti et al.

(10) Patent No.: US 8,785,187 B2
(45) Date of Patent: Jul. 22, 2014

(54) NEURAL STEM CELLS

(75) Inventors: Luciano Conti, Milan (IT); Steven Michael Pollard, Edinburgh (GB); Austin Gerard Smith, Edinburgh (GB)

(73) Assignee: The University Court of the University of Edinburgh, Edinburgh (GB)

(*) Notice: Subject to any disclaimer, the term of this patent is extended or adjusted under 35 U.S.C. 154(b) by 545 days.

(21) Appl. No.: 11/148,431

(22) Filed: Jun. 9, 2005

(65) Prior Publication Data

US 2006/0014281 A1 Jan. 19, 2006

(30) Foreign Application Priority Data

| Jun. 9, 2004 | (GB) | .................................. | 0412887.2 |
| Feb. 14, 2005 | (GB) | .................................. | 0503044.0 |
| Mar. 17, 2005 | (GB) | .................................. | 0505510.8 |

(51) Int. Cl.
*C12N 5/071* (2010.01)
*C12N 5/00* (2006.01)
*C12N 5/02* (2006.01)

(52) U.S. Cl.
USPC ............................ 435/368; 435/377; 435/375

(58) Field of Classification Search
USPC .................................................. 435/368, 375
See application file for complete search history.

(56) References Cited

U.S. PATENT DOCUMENTS

| 4,753,635 | A | 6/1988 | Sagen et al. |
| 4,980,174 | A | 12/1990 | Sagen et al. |
| 5,082,670 | A | 1/1992 | Gage et al. |
| 5,166,065 | A | 11/1992 | Williams et al. |
| 5,175,103 | A | 12/1992 | Lee et al. |
| 5,182,111 | A | 1/1993 | Aebischer et al. |
| 5,356,807 | A | 10/1994 | Blass et al. |
| 5,411,883 | A | 5/1995 | Boss et al. |
| 5,453,357 | A | 9/1995 | Hogan |
| 5,580,777 | A | 12/1996 | Bernard et al. |
| 5,589,376 | A | 12/1996 | Anderson et al. |
| 5,612,211 | A | 3/1997 | Wilson et al. |
| 5,672,499 | A | 9/1997 | Anderson et al. |
| 5,688,692 | A | 11/1997 | Jat et al. |
| 5,690,926 | A | 11/1997 | Hogan |
| 5,750,376 | A | 5/1998 | Weiss et al. |
| 5,753,505 | A | 5/1998 | Luskin |
| 5,753,506 | A | 5/1998 | Johe et al. |
| 5,843,780 | A | 12/1998 | Thomson |
| 5,851,832 | A | 12/1998 | Weiss et al. |
| 5,968,829 | A | 10/1999 | Carpenter |
| 5,980,885 | A | 11/1999 | Weiss et al. |
| 6,200,806 | B1 | 3/2001 | Thomson |
| 6,251,669 | B1 | 6/2001 | Luskin |
| 6,294,346 | B1* | 9/2001 | Weiss et al. .................. 435/7.21 |
| 6,361,996 | B1* | 3/2002 | Rao et al. ....................... 435/353 |
| 6,497,872 | B1 | 12/2002 | Weiss et al. |
| 6,498,018 | B1 | 12/2002 | Carpenter |
| 6,642,048 | B2 | 11/2003 | Xu et al. |
| 6,734,015 | B1 | 5/2004 | Rao et al. |
| 6,777,233 | B2 | 8/2004 | Carpenter |
| 6,787,353 | B1 | 9/2004 | Rao et al. |
| 6,800,480 | B1 | 10/2004 | Bodnar et al. |
| 6,812,027 | B2 | 11/2004 | Goldman et al. |
| 6,852,532 | B2 | 2/2005 | Mayer-Proschel et al. |
| 7,211,434 | B2* | 5/2007 | Van Der Kooy et al. ..... 435/377 |
| 7,531,354 | B2 | 5/2009 | Stice et al. |
| 7,968,337 | B2 | 6/2011 | Bruestle |
| 2002/0064873 | A1* | 5/2002 | Yang et al. ..................... 435/325 |
| 2002/0068045 | A1* | 6/2002 | Reubinoff et al. ............ 424/93.7 |
| 2003/0008392 | A1 | 1/2003 | Thomson |
| 2003/0032181 | A1* | 2/2003 | Weiss et al. .................... 435/368 |
| 2003/0059414 | A1* | 3/2003 | Ho et al. ...................... 424/93.21 |
| 2003/0211087 | A1* | 11/2003 | Goldman ................... 424/93.21 |
| 2004/0071672 | A1 | 4/2004 | Hogan |
| 2004/0107454 | A1 | 6/2004 | Wheeler et al. |

FOREIGN PATENT DOCUMENTS

| EP | 0 233 838 A2 | 8/1987 |
| EP | 1 489 163 A1 | 12/2004 |
| JP | 10-509592 A | 9/1998 |
| JP | 2001-526884 A | 12/2001 |
| JP | 2002-34580 A | 2/2002 |
| WO | WO 89/03872 A1 | 5/1989 |
| WO | WO 90/06757 A1 | 6/1990 |
| WO | WO 91/02003 A1 | 2/1991 |
| WO | WO 91/09936 A1 | 7/1991 |
| WO | WO 91/17242 A1 | 11/1991 |
| WO | WO 93/01275 A1 | 1/1993 |
| WO | WO 93/09802 A2 | 5/1993 |

(Continued)

OTHER PUBLICATIONS

Marchal-Victorion S, Deleyrolle L, De Weille J, Saunier M, Dromard C, Sandillon F, Privat A, Hugnot JP.The human NTERA2 neural cell line generates neurons on growth under neural stem cell conditions and exhibits characteristics of radial glial cells.Mol Cell Neurosci. Sep. 2003;24(1):198-213.*
Enzo Lifesciences, Product flier, Nov. 1, 2009.*
Citri and Yarden, Nature Reviews, Molecular Cell Biology, 7:505-516, 2006.*
Bazán, E., et al., "In vitro and in vivo characterization of neural stem cells," *Histol. Histopathol* 19:1261-1275, University of Murcia (Oct. 2004).
Gritti, A., et al., "Epidermal and Fibroblast Growth Factors Behave as Mitogenic Regulators for a Single Multipotent Stem Cell-Like Population from the Subventricular Region of the Adult Mouse Forebrain," *J. Neurosci.* 19:3287-3297, Society for Neuroscience (1999).

(Continued)

*Primary Examiner* — Valarie Bertoglio
(74) *Attorney, Agent, or Firm* — Sterne, Kessler, Goldstein & Fox P.L.L.C.

(57) ABSTRACT

A homogenous, symmetrically dividing population of adherent neural stem cells is obtained from ES cells or foetal or adult brain isolates, using an activator of a signalling pathway downstream of a receptor of the EGF receptor family, optionally in combination with an activator of a signalling pathway downstream of an FGF receptor. The neural stem cell population is highly pure and retains the ability to differentiate into neurons after in excess of 100 passages.

12 Claims, 14 Drawing Sheets

(56) References Cited

FOREIGN PATENT DOCUMENTS

| WO | WO 94/03199 A1 | 2/1994 |
|---|---|---|
| WO | WO 94/16718 A1 | 8/1994 |
| WO | WO 96/15226 A1 | 5/1996 |
| WO | WO 00/17323 A1 | 3/2000 |
| WO | WO 01/30981 A1 | 5/2001 |
| WO | WO 01/42421 A2 | 6/2001 |
| WO | WO 01/88104 A2 | 11/2001 |
| WO | WO 03/008566 A1 | 1/2003 |
| WO | WO 03/097812 A2 | 11/2003 |
| WO | WO 03/104444 A1 | 12/2003 |
| WO | WO 2004/050865 A1 | 6/2004 |
| WO | WO 2006/044204 A2 | 4/2006 |

OTHER PUBLICATIONS

Conti, L., et al., "Niche-Independent Symmetrical Self-Renewal of a Mammalian Tissue Stem Cell," *PLOS Biology* 3:1594-1606, Public Library of Science (Sep. 2005).

Maric, D., et al., "Prospective Cell Sorting of Embryonic Rat Neural Stem Cells and Neuronal and Glial Progenitors Reveals Selective Effects of Basic Fibroblast Growth Factor and Epidermal Growth Factor on Self-Renewal and Differentiation," *J. Neurosci.* 23:240-251, Society for Neuroscience (Jan. 2003).

Nakayama, T., et al., "Efficient production of neural stem cells and neurons from embryonic stem cells," *NeuroReport* 15:487-491, Karger Publishers (Mar. 2004).

Ostenfeld, T. and Svendsen, C.N., "Requirement for Neurogenesis to Proceed through the Division of Neuronal Progenitors following Differentiation of Epidermal Growth Factor and Fibroblast Growth Factor-2-Responsive Human Neural Stem Cells," *Stem Cells* 22:798-811, AlphaMed Press (Sep. 2004).

Vescovi, A.L., et al., "Isolation and Cloning of Multipotential Stem Cells from the Embryonic Human CNS and Establishment of Transplantable Human Neural Stem Cell Lines by Epigenetic Stimulation," *Exp. Neurol.* 156:71-83, Academic Press (1999).

Ying, Q.-L., et al., "Conversion of embryonic stem cells into neuroectodermal precursors in adherent monoculture," *Nat. Biotechnol.* 21:183-186, Nature Publishing Group (Published online Jan. 2003).

Ahmad, I., et al., "In vitro analysis of a mammalian retinal progenitor that gives rise to neurons and glia," *Brain Res.* 831:1-10, Elsevier Science B.V. (1999).

Chalmers-Redman, R.M.E., et al., "In vitro Propagation and Inducible Differentiation of Multipotential Progenitor Cells from Human Fetal Brain," *Neuroscience* 76:1121-1128, Pergamon Press (1997).

Doetsch, F., et al., "EGF Converts Transit-Amplifying Neurogenic Precursors in the Adult Brain into Multipotent Stem Cells," *Neuron* 36:1021-1034, Cell Press (2002).

Duittoz, A.H. and Hevor, T., "Primary culture of neural precursors from the ovine central nervous system (CNS)," *J. Neurosci, Meth.* 107:131-140, Elsevier Science B.V. (2001).

Gregg, C. and Weiss, S., "Generation of Functional Radial Glial Cells by Embryonic and Adult Forebrain Neural Stem Cells," *J. Neurosci.* 23:11587-11601, Society for Neuroscience (Dec. 2003).

Gritti, A., et al., "Multipotentneural Stem Cells Reside in the Rostral Extension and Olfactory Bulb of Adult Rodents," *Seminar*, Nov. 11, Program No. 134.6, ScholarOne, one page (2001).

Heins, N., et al., "Glial cells generate neurons: the role of the transcription factor Pax6," *Nat. Neurosci.* 5:308-315, Nature Publishing Group (2002).

Kojima, A. and Tator, C.H., "Epidermal Growth Factor and Fibroblast Growth Factor 2 Cause Proliferation of Ependymal Precursor Cells in the Adult Rat Spinal Cord in Vivo," *J. Neuropathol. Exp. Neurol.* 59:687-697, American Association of Neuropathologists Inc. (2000).

Liour, S.S. and Yu, R.K., "Differentiation of Radial Glia-Like Cells From Embryonic Stem Cells," *Glia* 42:109-117, Wiley-Liss, Inc. (Apr. 2003).

Merkle, F.T., et al., "Radial glia give rise to adult neural stem cells in the subventricular zone," *Proc. Natl. Acad. Sci. USA* 101:17528-17532, National Academy of Sciences (Dec. 2004).

Morest, D.K. and Silver, J., "Precursors of Neurons, Neuroglia, and Ependymal Cells in the CNS: What Are They? Where Are They From? How Do They Get Where They Are Going?," *Glia* 43:6-18, Wiley-Liss, Inc. (Jul. 2003).

Reynolds, B.A. and Weiss, S., "Generation of Neurons and Astrocytes from Isolated Cells of the Adult Mammalian Central Nervous System," *Science* 255:1707-1710, American Association for the Advancement of Science (1992).

Reynolds, B.A., et al., "A multipotent EGF-Responsive Striatal Embryonic Progenitor Cell Produces Neurons and Astrocytes," *J. Neurosci.* 12:4565-4574, Society for Neuroscience (1992).

Reynolds, B.A. and Weiss, S., "Clonal and Population Analyses Demonstrate That an EGF-Responsive Mammalian Embryonic CNS Precursor is a Stem Cell," *Develop. Biol.* 175:1-13, Academic Press, Inc. (1996).

Reitze, R.L., et al., "Purification of a pluripotent neural stem cell from the adult mouse brain," *Nature* 412:736-739, Nature Publishing Group (2001).

Tanigaki, K., et al., "Notch1 and Notch3 Instructively Restrict bFGF-Responsive Multipotent Neural Progenitor Cells to an Astroglial Fate," *Neuron* 29:45-55, Cell Press (2001).

Taupin, P., et al., "FGF-2-Responsive Neural Stem Cell Proliferation Requires CCg, a Novel Autocrine/Paracrine Cofactor," *Neuron* 28:385-397, Cell Press (2000).

Tropepe, V., et al., "Direct Neural Fate Specification from Embryonic Stem Cells: A Primitive Mammalian Neural Stem Cell Stage Acquired through a Default Mechanism," *Neuron* 30:65-78, Cell Press (2001).

Zhou, F.C. and Chiang, Y.H., "Long-term nonpassaged EGF-responsive neural precursor cells are stem cells," *Wound Rep. Reg.* 6:337-348, Blackwell Science (1998).

Akerud, P., et al., "Neuroprotection through Delivery of Glial Cell Line-Derived Neurotrophic Factor by Neural Stem Cells in a Mouse Model of Parkinson's Disease," *The Journal of Neuroscience* 21:8108-8118, Society for Neuroscience, United States (2001).

Akiyama, Y., et al., "Transplantation of Clonal Neural Precursor Cells Derived from Adult Human Brain Establishes Functional Peripheral Myelin in the Rat Spinal Cord," *Experimental Neurology* 167:27-39, Academic Press, London (2001).

Almazan, G., et al., "Epidermal Growth Factor and Bovine Growth Hormone Stimulate Differentiation and Myelination of Brain Cell Aggregates in Culture," *Developmental Brain Research* 21:257-264, Elsevier Science Publishers B.V., The Netherlands (1985).

Anchan, R.M. and Reh, T.A., "Trophic Factors Influence Proliferation of Germinal Neuroepithelial Cells of the Retina," *The Journal of Cell Biology* 109:58a, Abstract No. 308, Rockefeller University Press, United States (1989).

Anchan, R.M., et al., "EGF and TGF-α Stimulate Retinal Neuroepithelial Cell Proliferation In Vitro," *Neuron* 6:923-936, Cell Press, United States (1991).

Andres, F., "Removal and Reimplantation of the Parietal Cortex of Mice During the First Nine Days of Life: Consequences for the Barrelfield," *Journal of Neural Transplantation* 1:11-22, Hindawi Publishing Corporation, Egypt (1989).

Baetge, E.E., et al., "Neural Stem Cells for CNS Transplantation," *Annals of the New York Academy of Sciences* 695:285-291, The New York Academy of Sciences, United States (1993).

Bartlett, P.F., et al., "Immortalization of Mouse Neural Precursor Cells by the c-*myc* Oncogene," *Proc. Natl. Acad. Sci. USA* 85):3255-3259, National Academy of Sciences, United States (1988).

Bayer, S., "Neuron Production in the Hippocampus and Olfactory Bulb of the Adult Rat Brain: Addition or Replacement?," *Annals of the New York Academy of Sciences* 457:163-172, The New York Academy of Sciences, United States (1985).

Bernard, O., et al., "Role of the c-*myc* and the N-*myc* Proto-Oncogenes in the Immortalization of Neural Precursors," *Journal of Neuroscience Research* 24:9-20, Alan R. Liss, Inc, United States (1989).

(56) References Cited

OTHER PUBLICATIONS

Björklund, A. and Gage, F.H., "Neural Grafting in Animal Models of Neurodegenerative Diseases," *Annals of the New York Academy of Sciences 457*:53-81, The New York Academy of Sciences, United States (1985).
Blakemore, W.F. and Crang, A.J., "Extensive Oligodendrocyte Remyelination following Injection of Cultured Central Nervous System Cells into Demyelinating Lesions in Adult Central Nervous System," *Dev. Neurosci. 10*:1-11, Karger AG, Basel (1988).
Bossart, E. and Conti, G., "Epidermal Growth Factor Stimulates Colony Formation and Non-Neuronal Marker Protein Expression by Human Neuroblastoma in Methylcellulose Culture," *Anticancer Research 9*: 1497-1504, International Institute of Anticancer Research (1989).
Bouvier, M.M. and Mytilineou, C., "Basic Fibroblast Growth Factor (bFGF) Promotes the Survival and Proliferation of Mesencephalic Neuronal Precursors In Vitro," *Society for Neuroscience Abstracts 18*: Abstract No. 403.7, Society for Neuroscience, United States (1992).
Boyles, J.K., et al., "Accumulation of Apolipoproteins in the Regenerating and Remyelinating Mammalian Peripheral Nerve," *The Journal of Biological Chemistry 265*: 17805-17815, The American Society for Biochemistry and Molecular Biology, Inc., United States (1990).
Bray, G.M., "Neural Transplantation," *Current Opinion in Neurology and Neurosurgery 3*:926-933, Current Science Ltd., United States (1990).
Bredesen, D.E., et al., "Neural Transplantation Using Temperature-sensitive Immortalized Neural Cell: A Preliminary Report," *Annals of Neurology 27*:205-207, American Neurological Society, United States (1990).
Brickman, Y.G., et al., "Heparan Sulfates Mediate the Binding of Basic Fibroblast Growth Factor to a Specific Receptor on Neural Precursor Cells," *The Journal of Biological Chemistry 270*:24941-24948, The American Society for Biochemistry and Molecular Biology, Inc., United States (1995).
Brüstle, O., et al., "Chimeric brains generated by intraventricular transplantation of fetal human brain cells into embryonic rats," *Nature Biotechnology 16*:1040-1044, Nature Publishing Group, England (1998).
Calof, A.L. and Chikaraishi, D.M., et al., "Analysis of Neurogenesis in a Mammalian Neuroepithelium: Proliferation and Differentiation of an Olfactory Neuron Precursor In Vitro," *Neuron 3*: 115-127, Cell Press, United States (1989).
Calof, A.L., et al., "Regulation of Neurogenesis and Neuronal Differentiation in Primary and Immortalized Cells from Mouse Olfactory Epithelium," *J. Cell Biology 109*:57a, Abstracts of the American Society for Cell Biology 29th Annual Meeting, The Rockefeller University Press, United States (1989).
Cattaneo, E. and McKay, R., "Identifying and Manipulating Neuronal Stem Cells," *Trends in Neurosciences 14*: 338-340, Elsevier Science Publishers Ltd., United Kingdom (1991).
Cattaneo, E. and McKay, R., "Proliferation and Differentiation of Neuronal Stem Cells Regulated by Nerve Growth Factor," *Nature 347*:762-765, Nature Publishing Group, England (1990).
Cattaneo, E., et al., "Non-virally Mediated Gene Transfer into Human Central Nervous System Precursor Cells," *Molecular Brain Research 42*: 161-166, Elsevier Science BV, The Netherlands (1996).
Cepko, C.L., "Immortalization of Neural Cells via Retrovirus-Mediated Oncogene Transduction," *Ann. Rev. Neurosci. 12*:47-65, Annual Reviews Inc, United States (1989).
Cortez, S.C., et al., "Experimental Fluid Percussion Brain Injury: Vascular Disruption and Neuronal and Glial Alterations," *Brain Research 482*:271-282, Elsevier Science Publishers B.V., The Netherlands (Mar. 1989).
Cotter, T., et al., "The Induction of Apoptosis by Chemotherapeutic Agents Occurs in All Phases of the Cell Cycle," *Anticancer Research 12*:773-780, International Institute of Anticancer Research (1992).
Dahlstrand, J., et al., "Nestin mRNA Expression Correlates with the Central Nervous System Progenitor Cell State in Many, but not all, Regions of Developing Central Nervous System," *Developmental Brain Research 84*:109-129, Elsevier Science Publishers, The Netherlands (1995).
Date, I., et al., "MPTP-treated Young Mice but not Aging Mice Show Partial Recovery of the Nigrostriatal Dopaminergic System by Stereotaxic Injection of Acidic Fibroblast Growth Factor (aFGF)," *Brain Research 526*:156-160, Elsevier Science Publishers BV, The Netherlands (1990).
Deloulme, J.C., et al., "Establishment of Pure Neuronal Cultures from Fetal Rat Spinal Cord and Proliferation of the Neuronal Precursor Cells in the Presence of Fibroblast Growth Factor," *Journal of Neuroscience Research 29*:499-509, Wiley-Liss, Inc., United States (1991).
Drago, J., et al., "Fibroblast Growth Factor-mediated Proliferation of Central Nervous System Precursors Depends on Endogenous Production of Insulin-like Growth Factor I," *Proc. Natl. Acad. Sci. USA 88*:2199-2203, National Academy of Sciences, United States (1991).
Dunnett, S.B., et al, "Dopamine-rich Transplants in Experimental Parkinsonism," *Trends in Neurosciences 6*:266-270, Elsevier Science Publishers B.V., United States (1983).
Emerich, D.F., et al., "Behavioral Effects of Neural Transplantation," *Cell Transplantation 1*: 401-427, Pergamon Press Ltd., United States (1992).
Evrard, C., et al., "Immortalization of Bipotential and Plastic Glio-neuronal Precursor Cells," *Proc. Natl. Acad. Sci. USA 87*:3062-3056, National Academy of Sciences, United States (1990).
Faaland, C.A., et al., "Rapid Uptake of Tyrphostin into A431 Human Epidermoid Cells is Followed by Delayed inhibition of Epidermal Growth Factor (EGF)-Stimulated EGF Receptor Tyrosine Kinase Activity," *Molecular and Cellular Biology 11*:2697-2703, American Society for Microbiology, United States (1991).
Federoff, H.J., et al., "Expression of Nerve Growth Factor In Vivo from a Defective Herpes Simplex Virus 1 Vector Prevents Effects of Axotomy on Sympathetic Ganglia," *Proc. Natl. Acad. Sci. USA 89*:1636-1640, National Academy of Sciences, United States (1992).
Ferguson, I.A. and Johnson, E.M., "Fibroblast Growth Factor Receptor-bearing Neurons in the CNS: Identification by Receptor-mediated retrograde Transport," *The Journal of Comparative Neurology 313*:693-706, Wiley-Liss, Inc., United States (1991).
Ferrrari, G., et al., "Basic Fibroblast Growth Factor Promotes the Survival and Development of Mesencephalic Neurons n Culture," *Developmental Biology 133*:140-147, Academic Press, Inc., United States (1989).
Flax, J.D., et al., "Engraftable Human Neural Stem Cells Respond to Developmental Cues, Replace Neurons, and Express Foreign Genes," *Nature Biotechnology 16*:1033-1039, Nature Publishing Group, England (1998).
Franklin, M., et al., "Transplanted Type-1 Astrocytes Facilitate Repair of Demyelination Lesions by Host Oligodendrocytes in Adult Rat Spinal Cord," *Neuropathol. Appl. Neurobiol. 17*:244, 81st meeting of British Neuropathological Society (1991).
Frederiksen, K. and McKay, R.D.G., "Proliferation and Differentiation of Rat Neuroepithelial Precursor Cells In Vivo," *The Journal of Neurosciences 8*:1144-1151, Society for Neurosciences, United States (1988).
Frederiksen, K., et al., "Immortal Neuroepithelial Precursor Cell Lines," *Society for Neuroscience Abstracts 13*:182, Abstract No. 55.6, Society for Neuroscience, United States (1987).
Frederiksen, K., et al., "Immortalization of Precursor Cells from the Mammalian CNS," *Neuron 1*:439-448, Cell Press, United States (1988).
Freed, C.R., et al., "Transplantation of Human Fetal Dopamine Cells for Parkinson's Disease," *Arch. Neurol. 47*:505-512, American Medical Association, United States (1990).
Freshney, R., "Culture of Animal Cells: A Manual of Basic Technique," *Second Edition*: 137-153, Chapter 11, Wiley-Liss Inc., United States (1992).
Freshney, R.I., "Culture of Animal Cells: A Manual of Basic Technique," *Second Edition*: 190-195, Chapter 14, Alan R. Liss, Inc, United States (1992).
Fricker, R.A., et al., "Site-specific Migration and Neuronal Differentiation of Human Neural Progenitor Cells after Transplantation in the

(56) References Cited

OTHER PUBLICATIONS

Adult Rat Brain," *The Journal of Neuroscience 19*:5990-6005, Society for Neuroscience, United States (1999).

Friedmann, T., "Gene Therapy for Neurological Disorders," *Trends in Genetics 10*:210-214, Elsevier Science Ltd., England (1994).

Fults, D., et al., "Establishment and Characterization of a Human Primitive Neuroectodermal Tumor Cell Line from the Cerebral Hemisphere," *Journal of Neuropathology and Experimental Neurology 51*:272-280, The American Association of Neuropathologists (1992).

Geller, A.I. and Breakefield, X.O., "A Defective HSV-1 Vector Expresses *Esherichia coli* β—Galactosidase in Cultured Peripheral Neurons," *Science 241*: 1667-1669, American Association for the Advancement of Science, United States (1988).

Gensburger, C., et al., "Brain Basic Fibroblast Growth Factor Stimulates the Proliferation of Rat Neuronal Precursor Cells In Vitro," *FEBS Lett 217*(1): 1-5, Elsevier Science Publishers B.V., The Netherlands (1987).

Godfraind, C., et al., "In Vivo Analysis of Glial Cell Phenotypes During a Viral Demyelinating Disease in Mice," *The Journal of Cell Biology 109*:2405-2416, Rockefeller University Press, United States (1989).

Goetz, C.G., et al., "United Parkinson Foundation Neurotransplantation Registry on Adrenal Medullary Transplants: Presurgical, and 1- and 2-Year Follow-up," *Neurology 41*:1719-1722, American Academy of Neurology, United States (1991).

Groves, A.K., et al., "Repair of Demyelinated Lesions by Transplantation of Purified O-2A Progenitor Cells," *Nature 362*: 453-455, Nature Publishing Group, England (1993).

Guentert-Lauber, B. and Honegger, P., "Responsiveness of Astrocytes in Serum-Free Aggregate Cultures to Epidermal Growth Factor: Dependence on the Cell Cycle and the Epidermal Growth Factor Concentration," *Dev.Neurosci.7*:286-295, S. Karger AG, Basel (1985).

Hall, P.A. and Watt, F.M., "Stem Cells: the Generation and Maintenance of Cellular Diversity," *Development 106*:619-633, Company of Biologists Limited, England (1989).

Hammang, J.P., et al., "Myelination Following Transplantation of EGF-Responsive Neural Stem Cells into a Myelin-Deficient Environment," *Experimental Neurology 147*:84-95, Academic Press, Inc., United States (1997).

Hammang, J.P., et al., "Transplantation of Epidermal Growth Factor-Responsive Neural Stem Cell Progeny into the Murine Central Nervous System," *Methods in Neurosciences 21*:281-293, Academic Press Inc, United States (1994).

Heikkila, R.E. and Sonsalla, P.K., "The Use of the MPTP-Treated Mouse as an Animal Model of Parkinsonism," *Can. J. Neurol. Sci. 14*:436-440, Canadian Journal of Neurological Sciences, Canada (1987).

Hockfield, S. and McKay, R.D.G., "Identification of Major Cell Classes in the Developing Mammalian Nervous System," *The Journal of Neuroscience 5*: 3310-3328, Society for Neuroscience, United States (1985).

Hodgson, C.P., "Patent Update: Biologicals & Immunologicals: Advances in Vector Systems for Gene Therapy," *Exp. Opin. Ther. Patents 5*:459-468, Ashley Publications Ltd., United Kingdom (1995).

Hoffman, D., et al., "Transplantation of a Polymer-Encapsulated Cell Line Genetically Engineered to Release NGF," *Experimental Neurology 122*: 100-106, Academic Press, Inc., United States (1993).

Hollenberg, M.D. and Cuatrecasas, P., "Epidermal Growth Factor: Receptors in Human Fibroblasts and Modulation of Action by Cholera Toxin," *Proc. Natl. Acad. Sci. USA 70*:2964-2968, The National Academy of Sciences, United States (1973).

Hunter, S.F. and Bottenstein, J.E., "Growth Factor Responses of Enriched Bipotential Glial Progenitors," *Developmental Brain Research 54*:235-248, Elsevier Science Publishers BV, The Netherlands (1990).

Hurtig, H., et al., "Postmortem Analysis of Adrenal-Medulla-to-Caudate Autograft in a Patient with Parkinson's Disease," *Annals of Neurology 25*(6): 607-614, American Neurological Association, United States (1989).

Isacson, O., et al., "A Primate Model of Huntington's Disease: Cross-Species Implantation of Striatal Precursor Cells to the Excitotoxically Lesioned Baboon Caudate-Putamen," *Exp. Brain Res. 75*:213-220, Springer-Verlag, United States (1989).

Jackowski, A., "Neural Injury Repair: Hope for the Future as Barriers to Effective CNS Regeneration become Clearer," *British Journal of Neurosurgery 9*:303-317, The Neurological Foundation, United Kingdom (1995).

Jänisch, V.W. and Grieshammer, T., "Expression of Immunohistochemical Differentiation Markers in Normal and Transformed Neoplastic Neuroectodermal Stem Cells," *Acta Histochemica 42*:139-147, Elsevier BV, The Netherlands (1992).

Jiao, S., et al., "Intracerebral Transplants of Primary Muscle Cells: A Potential 'Platform' for Transgene Expression in the Brain," *Brain Research 575*: 143-147, Elsevier Science Publishers BV, The Netherlands (1992).

Kamholz, J., et al., "Identification of Three Forms of Human Myelin Basic Protein by cDNA Cloning," *Proc. Natl. Acad. Sci. USA 83*:4962-4966, National Academy of Sciences, United States (1996).

Kaplan, M.S., "Neurogenesis in the 3-Month-Old Rat Visual Cortex," *The Journal of Comparative Neurology 195*:323-338, Alan R. Liss, Inc., United States (1981).

Kawaja, M.D., et al., "Somatic Gene Transfer of Nerve Growth Factor Promotes the Survival of Axotomized Septal Neurons and the Regeneration of Their Axons in Adult Rats," *The Journal of Neuroscience 12*:2849-2864, Society for Neuroscience, United States (1992).

Kesslak, J.P., et al., "Adult and Embryonic Frontal Cortex Transplants after Frontal Cortex Ablation Enhance Recovery on a Reinforced Alternation Task," Experimental Neurology 94: 615-626, Academic Press, Inc., United States (1986).

Korr, H., et al., "Autoradiographic Investigations of Glial Proliferation in the Brain of Adult Mice. I. The DNA synthesis phase of neuroglia and endothelial cells," *J. Comp. Neur. 150*:169-175, The Wistar Institute Press, United States (1973).

Kumar, S., et al., "Identification of a Set of Genes with Developmentally Down-Regulated Expression in the Mouse Brain," *Biochemical and Biophysical Research Communications 185*:1155-1161, Academic Press, Inc., United States (1992).

Lendahl, U., et al., "CNS Stem Cells Express a New Class of Intermediate Filament Protein," *Cell 60*: 585-595, Cell Press, United States (1990).

Lin, L.-F.H., et al., "GDNF: A Glial Cell Line-Derived Neurotrophic Factor for Midbrain Dopaminergic Neurons," *Science 260*:1130-1132, American Association for the Advancement of Science, United States (1993).

Lindvall, O., et al., "Grafts of Fetal Dopamine Neurons Survive and Improve Motor Function in Parkinson's Disease," *Science 247*(4942): 574-577, American Association for the Advancement of Science, United States (1990).

Lindvall, O., et al., "Human Fetal Dopamine Neurons Grafted into the Striatum in Two Patients with Severe Parkinson's Disease a Detailed Account of Methodology and a 6-month Follow-up," *Arch. Neurol. 46*:615-631, American Medical Association, United States (1989).

Lo, L.-C., et al., "V-*myc* Immortalization of Early Rat Neural Crest Cells Yields a Clonal Cell Line Which Generates Both Glial and Adrenergic Progenitor Cells," *Developmental Biology 145*:139-153, Academic Press, Inc., United States (1991).

Lois, C. and Alvarez-Buylla, A., "Migration of Neuroblasts from the Lateral Ventricle to the Olfactory Bulb in the Adult Mammalian CNS," *Society for Neuroscience Abstracts 19*: 873, Abstract No. 361.6, Society for Neuroscience, United States (1993).

Lubetzki, C., et al., "Gene Transfer of Rat Mature Oligodendrocytes and Glial Progenitor Cells with the LacZ Gene," *Annals of the New York Academy of Sciences 605*: 66-70, New York Academy of Sciences, United States (1990).

Luskin, M.B., et al., "Rate and Pattern of Migration of Olfactory Bulb Interneurons Generated Postnatally in the Subventricular Zone,"

(56) References Cited

OTHER PUBLICATIONS

*Society for Neuroscience Abstracts 19*: 873, Abstract No. 361.9, Society for Neuroscience, United States (1993).

Mantel, C., et al., "Macrophage Inflammatory Protein-1α Enhances Growth Factor-Stimulated Phosphatidylcholine Metabolism and Increases cAMP Levels in the Human Growth Factor-Dependent Cell Line M07e, Events Associated with Growth Suppression," *The Journal of Immunology 154*:2342-2350, The American Association of Immunologists, United States (1995).

Masters, B.A., et al., "Insulin-like Growth Factor I(IGF-I) Receptors and IGF-I Action in Oligodendrocytes from Rat Brains," *Regulatory Peptides 33*:117-131, Elsevier BV, The Netherlands (1991).

McDermott, A.M., et al., "Thyrotropin Releasing Hormone (TRH) and a Degradation Stabilized Analogue (RX77368) Stimulate Phosphoinositide Turnover in Cultured Astrocytes in a Regionally Specific Manner," *Neurochem. Int. 20*:307-313, Pergamon Press plc, United States (1992).

McKay, R., "Stem Cells in the Central Nervous Systems," *Science 276*:66-71, American Association for the Advancement of Science, United States (1997).

McKeon, R.J., et al., "Reduction of Neurite Outgrowth in a Model of Glial Scarring Following CNS Injury is Correlated with the Expression of Inhibitory Molecules on Reactive Astrocytes," *The Journal of Neuroscience 11*:3398-3411, Society for Neuroscience, United States (1991).

McKinnon, R.D., et al., "FGF Modulates the PDGF-driven Pathway of Oligodendrocyte Development," *Neuron 5*:603-614, Cell Press, United States (1990).

Mehler, M.F. and Kessler, J.A., "Progenitor Cell Biology: Implications for Neural Regeneration," *Arch. Neurol. 56*:780-784, American Medical Association, United States (1999).

Metcalf, D., "The Hemopoietic Regulators—An Embarrassment of Riches," *BioEssays 14*:799-805, Cambridge University Press, United Kingdom (1992).

Micci, M.-A., et al., "Neural Stem Cells Express RET, Produce Nitric Oxide, and Survive Transplantation in the Gastrointestinal Tract," *Gastroenterology 121*:757-766, The American Gastroenterological Association (2001).

Milward, E.A., et al., "Isolation and Transplantation of Multipotential Populations of Epidermal Growth Factor-Responsive, Neural Progenitor Cells From the Canine Brain," *J. Neurosci. Res. 50*:862-871, Wiley-Liss, Inc., United States (1997).

Monnet-Tschudi, F. and Honegger, P., "Influence of Epidermal Growth Factor on the Maturation of Fetal Rat Brain Cells in Aggregate Culture," *Dev. Neurosci. 11*: 30-40, S. Karger AG, Basel (1989).

Morrison, R., et al., "Trophic Stimulation of Cultured Neurons from Neonatal Rat Brain by Epidermal Growth Factor," *Science 238*: 72-75, American Association for the Advancement of Science, United States (1987).

Morshead, C.M. and van der Kooy, D., "Postmitotic Death is the Fate of Constitutively Proliferating Cells in the Subependymal Layer of the Adult Mouse Brain," *The Journal of Neuroscience 12*:249-256, Society for Neuroscience, United States (1996).

Morshead, C., et al., "Neural Stem Cells are Located in the Subependymal Region of the Adult Mammalian Forebrain," *Society for Neuroscience Abstracts 19*: 870, Abstract No. 360.7, Society for Neuroscience, United States (1993).

Murphy, M., et al., "Fibroblast Growth Factor Stimulates the Proliferation and Differentiation of Neural Precursor Cells In Vitro," *Journal of Neuroscience Research 25*:463-475, Wiley-Liss, Inc., United States (1990).

Mytilineou, C., et al., "Epidermal Growth Factor-Induced Survival and Proliferation of Neuronal Precursor Cells from Embryonic Rat Mesencephalon," *Neuroscience Letters 135*: 62-66, Elsevier Science Publishers Ltd., Ireland (1992).

Nakafuku, M. and Kaziro, Y., "Epidermal Growth Factor and Transforming Growth Factor-α can Induce Neuronal Differentiation of Rat Pheochromocytoma PC12 Cells Under Particular Culture Conditions,"*FEBS 315*:227-232, Elsevier Science Publishers B.V., The Netherlands (1993).

Notter, M.F.D., et al., "Neuronal Properties of Monkey Adrenal Medulla In Vitro," *Cell Tissue Res. 244*:69-76, Springer-Verlag, Germany (1986).

Nurcombe, V., et al., "Developmental Regulation of Neural Response to FGF-1 and FGF-2 by Heparan Sulfate Proteoglycan," *Science 260*:103-106, American Association for the Advancement of Science, United States (1993).

Olson, L., "Grafts and Growth Factors in CNS," *Stereotact. Fund. Neurosurg. 54*:250-267, Karger AG, Basel (1990).

Orkin, S.H. and Motulsky, A.G., "Report and Recommendations of the Panel to Assess the NIH Investment in Research on Gene Therapy," National Institute of Health, United States (1995).

Palella, T.D., et al., "Expression of Human HPRT mRNA in Brains of Mice Infected with a Recombinant Herpes Simplex Virus-1 Vector," *Gene 80*:137-144, Elsevier Science Publishers B.V., The Netherlands (1989).

Pallage, V., et al., "Long-term Effects of Nerve Growth Factor and Neural Transplants on Behavior of Rats with Medial Septal Lesions," *Brain Research 386*:197-208, Elsevier, The Netherlands (1986).

Palmer, A.C., "Proceedings of the Eighty-first Meeting of the British Neuropathological Society held at the Institute of Psychiatry Jan. 10-11, 1991," *Neuropathology and Applied Neurobiology 17*: 239-258, John Wiley & Sons Inc., United Kingdom (1991).

Palmer, T.D., et al., "Genetically Modified Skin Fibroblasts Persist Long After Transplantation but Gradually Inactivate Introduced Genes," *Proc. Natl. Acad. Sci. USA 88*:1330-1334, National Academy of Sciences, United States (1991).

Paterson, J.A., "Dividing and Newly Produced Cells in the Corpus Callosum of Adult Mouse Cerebrum as Detected by Light Microscopic Radioautography," *Anat. Anz. 153*: 149-168, Elsevier, Germany (1983).

Perlow, M.J., et al., "Brain Grafts Reduce Motor Abnormalities Produced by Destruction of Nigrostriatal Dopamine System," *Science 204*:643-647, American Association for the Advancement of Science, United States (1979).

Pezzoli, G., et al., "Intraventricular Infusion of Epidermal Growth Factor Restores Dopaminergic Pathway in Hemiparkinsonian Rats," *Movement Disorders 6*:281-287, Movement Disorder Society, United States (1991).

Piescinski, P., et al., "Neurogenesis of the Amygdaloid Complex in the Rhesus Monkey," *Society for Neuroscience Abstracts 16*:1147, Society for Neuroscience, United States (1990).

Piszczkiewicz, S.J. and Hall, A.K., "Proliferation and Survival of Rat Sensory Neuron Precursors In Vitro," *Society for Neuroscience Abstracts 19*:1709, Society for Neuroscience, United States (1993).

Potten, C.S. and Loeffler, M., "Stem Cells: Attributes, Cycles, Spirals, Pitfalls and Uncertainties Lessons for and from the Crypt," *Development 110*:1001-1020, The Company of Biologists Limited, Great Britain (1990).

Price, J. and Thurlow, L., "Cell Lineage in the Rat Cerebral Cortex: A Study Using Retroviral-Mediated Gene Transfer," *Development 104*:473-482, The Company of Biologists Limited, Great Britain (1988).

Price, J. and Williams, B.P., "Neural Stem Cells," *Current Opinion in Neurobiology 11*:564-567, Elsevier Science Ltd., The Netherlands (2001).

Price, J., et al., "Cell Lineage in the Cerebral Cortex," *Development Supplement 2*:23-28, The Company of Biologists Limited, Great Britain (1991).

Pulliam, L., et al., "A Normal Human Brain Cell Aggregate Model for Neurobiological Studies," *Journal of Neuroscience Research 21*:521-530, Alan R. Liss, Inc., United States (1988).

Raff, M.C., et al., "A glial progenitor cell that develops in vitro into an astrocyte or an oligodendrocyte depending on culture medium," *Nature 303*:390-396, Nature Publishing Group, England (1983).

Rakic, P., "Limits of Neurogenesis in Primates," *Science 227*:1054-1056, American Association for the Advancement of Science, United States (1985).

Ramatowski, D., et al., "Laminin enhances proliferation and migration of EGF-Generated CNS stem cell progeny," *Society for Neuroscience Abstracts 19*: 870, Abstract No. 360.10, Society for Neuroscience, United States (1993).

(56) References Cited

OTHER PUBLICATIONS

Reh, T.A. and Kljavin, I.J. "Age of Differentiation Determines Rat Retinal Germinal Cell Phenotype: Induction of Differentiation by Dissociation," *Journal of Neuroscience 9*:4179-4189, Society for Neuroscience, United States (1989).

Renfranz, P.J., et al., "Region-Specific Differentiation of Hippocampal Stem Cell Line HiB5 upon Implantation into the Developing Mammalian Brain," *Cell 66*:713-729, Cell Press, United States (1991).

Reynolds, B.A. and Weiss, S., "A Non-Transformed, Growth Factor-Dependent Stem Cell Line Derived from the Embryonic Mouse CNS Produces Neurons, Astrocytes and Oligodendrocytes," *Restorative Neurology and Neuroscience 4*: 208, IOS Press, Amsterdam (1992).

Reynolds, B.A. and Weiss, S., "EGF-Responsive Stem Cells in the Mammalian Central Nervous System," *Neuronal Cell Death and Repair Chapter 19*: 247-256, Elsevier Science Publishers B.V., The Netherlands (1993).

Reynolds, B.A., et al., "EGF- and TGFα-Responsive Striatal Embryonic Progenitor Cells Produce both Neurons and Astrocytes," *Society for Neuroscience Abstracts 16*:1147, Society for Neuroscience, United States (1990).

Rezvani, M., et al., "Modification of Radiation Myelopathy by the Transplantation of Neural Stem Cells in the Rat," *Radiation Research 156*: 408-412, Radiation Research Society, United States (2001).

Richards, L.J., et al., "De novo Generation of Neuronal Cells from the Adult Mouse Brain," *Proc. Natl. Acad. Sci. 89*:8591-8595, National Academy of Sciences, United States (1992).

Richardson, W.D., et al., "A Role for Platelet-Derived Growth Factor in Normal Gliogenesis in the Central Nervous System," *Cell 53*: 309-319, Cell Press, United States (1988).

Robbins, "The Nervous System: Neuroglia," *Pathologic Basis of Disease*: 1373-1378, Saunders/Elsevier, United States (1984).

Rohrer, H., et al., "Proliferation and Differentiation of Neuronal Precursor Cells in the Chick Peripheral Nervous System," *Konferenz der Gesellschaft für biologische Chemie 368*:1290-1296 (1987).

Ronnett, G.V., et al., "Human Cortical Neuronal Cell Line: Establishment from a Patient with Unilateral Megalencephaly," *Science 248*:603-605, American Association for the Advancement of Science, United States (1990).

Rosenberg, M.B., et al., "Grafting Genetically Modified Cells to the Damaged Brain: Restorative Effect of NGF Expression," *Science 242*:1575-1578, American Association for the Advancement of Science, United States (1988).

Rudland, P.S., et al., "Growth Control in Cultured Mouse Fibroblasts: Induction of the Pleiotypic and Mitogenic Responses by a Purified Growth Factor," *Proc. Natl. Acad. Sci. USA 71*:2600-2604, The National Academy of Sciences, United States (1974).

Ryder, E.F., et al., "Establishment and Characterization of Multipoint Neural Cell Lines Using Retrovirus Vector-Mediated Oncogene Transfer," *Journal of Neurobiology 21*:356-375, John Wiley & Sons, Inc., United States (1990).

Sambrook, J., et al., "Molecular Cloning—A Laboratory Manual," 2:12.2-12.10, Cold Spring Harbour Laboratory Press, United States (1989).

Saneto, R.P., et al., "Insulin/Insulin-Like Growth Factor I and Other Epigenetic Modulators of Myelin Basic Protein Expression in Isolated Oligodendrocyte Progenitor Cells," *Journal of Neuroscience Research 21*: 210-219, Alan R. Liss, Inc., United States (1998).

Saneto, R., et al., "Neuronal and Glial Cells: Cell Culture of the Central Nervous System," *Neurochemistry: A Practical Approach* (eds. Turner, A. and Bachelard, H.): 27-63, Oxford University Press, United States (1987).

Sensenbrenner, M., et al., "Proliferation of Neuronal Precursor Cells from the Central Nervous System in Culture," *Reviews in the Neurosciences 5*:43-53, Freund Publishing House Ltd., England (1994).

Smart, I., "The Subependymal Layer of the Mouse Brain and its Cell Production as Shown by Radioautography after Thymidine-$H^3$ Injection," *The Journal of Comparative Neurology 116*:325-347, Wiley-Liss Inc, United States (1961).

Snyder, E.Y., et al., "Multipotent Neural Cell Lines Can Engraft and Participate in Development of Mouse Cerebellum," *Cell 68*:33-51, Cell Press, United States (1992).

Steinbusch, H.W.M., et al., "Basic Fibroblast Growth Factor Enhances Survival and Sprouting of Fetal Dopaminergic Cells Implanted in the Denervated Rat Caudate-Putamen: Preliminary Observations," *Progress in Brain Research 82*: 81-86, Elsevier Science Publishers B.V., The Netherlands (1990).

Stenevi, U., et al., "Effects of Localized Intracerebral Injections of Nerve Growth Factor on the Regenerative Growth of Lesioned Central Noradrenergic Neurones," *Brain Research 69*:217-234, Elsevier Scientific Publishing Company, The Netherlands (1974).

Stratagene Product Catalog, "Innovations in Molecular Biology" pp. 115-116, United States (1991).

Temple, S., "Division and Differentiation of Isolated CNS Blast Cells in Microculture," *Nature 340*:471-473, Nature Publishing Group, England (1989).

Toda, H., et al., "Grafting Neural Stem Cells Improved the Impaired Spatial Recognition in Ischemic Rats," *Neuroscience Letters 361*:9-12, Elsevier Science Ltd, Ireland (2001).

Tohyama, T., et al., "Nestin Expression in Embryonic Human Neuroepithelium and in Human Neuroepithelial Tumor Cells,"*Laboratory Investigation 66*:303-313, The United States and Canadian Academy of Pathology, Inc., United States (1992).

Travis, J., "The Search for Liver Stem Cells Picks Up," *Science 259*:1829-1829, American Association for the Advancement of Science, United States (1993).

van der Maazen, R., et al., "Radiosensitivity of Glial Progenitor Cells of the Perinatal and Adult Rat Optic Nerve Studied by an In vitro Clonogenic Assay," *Radiotherapy and Oncology 20*:258-624, Elsevier Science Publishers B.V., The Netherlands (1991).

Vescovi, A.L., et al., "Continual Proliferation of EGF-Dependent Progenitor Cells of the Embryonic Human CNS In Vitro," *Society for Neuroscience Abstracts 19*: 871, Abstract No. 360.12, Society for Neuroscience, United States (1993).

Villa, P., et al., "Synthesis of Specific Proteins in Trophic Factor-Deprived Neurons Undergoing Apoptosis," *J. Neurochem. 62*:1468-1475, Raven Press Ltd., United States (1994).

Walsh, C. and Cepko, C.L., "Clonally Related Cortical Cells Show Several Migration Patterns," *Science 241*:1342-1345, American Association for the Advancement of Science, United States (1988).

Watts et al., "Adrenal-Caudate Transplantation in Patients With Parkinson's Disease (PD):-1-Year Follow-up," *Neurology 39*(Suppl. 1):127, Abstract No. PP72, American Academy of Neurology, United States (1989).

Weiss, S., et al., "Multipotent CNS Stem Cells Are Present in the Adult Mammalian Spinal Cord and Ventricular Neuroaxis," *Proc. Nat'l. Acad. Sci. USA 16*:7599-7609, Society for Neuroscience, United States (1996).

Weiss, S., et al., "Synaptogenesis of Cultured Striatal Neurons in Serum-free Medium: A Morphological and Biochemical Study," *Proc. Nat'l. Acad. Sci. USA 83*:2238-2242, National Academy of Sciences , United States (1986).

Wendt, J.S., et al., "Regeneration of Rat Hippocampal Fimbria Fibers after Fimbria Transection and Peripheral Nerve or Fetal Hippocampal Implantation," *Experimental Neurology 79*:452-461, Academic Press Inc., United States (1983).

Widner, H., et al., "Bilateral Fetal Mesencephalic Grafting in Two Patients with Parkinsonism Induced by 1-Methyl-4-phenyl-1,2,3,6-tetrahydropyridine (MPTP)", *N. Engl. J. of Med. 327*:1556-1563, Massachusetts Medical Society, United States (1992).

Williams, G.T., "Programmed Cell Death: Apoptosis and Oncogenesis," *Cell 65*:1097-1098, Cell Press, United States (1991).

Williams, L.R., et al., "Continuous Infusion of Nerve Growth Factor Prevents Basal Forebrain Neuronal Death after Fimbria Fornix Transaction," *Proc. Nat'l. Acad. Sci. USA 83*:9231-9235, National Academy of Sciences, United States (1986).

Winkler, C., et al., "Incorporation and Glial Differentiation of Mouse EGF-Responsive Neural Progenitor Cells after Transplantation into the Embryonic Rat Brain," *Molecular and Cellular Neuroscience11*:99-116, Academic Press, United States (1998).

(56) References Cited

OTHER PUBLICATIONS

Wolff, J.A., et al., "Grafting Fibroblasts Genetically Modified to Produce L-dopa in a rat Model of Parkinson Disease," *Proc. Nat'l. Acad. Sci. USA 86*:9011-9014, National Academy of Sciences, United States (1989).

Wolswijk, G. and Noble, M., "Identification of an Adult-Specific Glial Progenitor Cell," *Development 105*:387-400, The Company of Biologists Limited, Great Britain (1989).

Yamada, K.M., et al., "Fibronectin in Cell Adhesion, Differentiation, and Growth," *Growth of Cells in Hormonally Defined Media Cold Spring Harbor Conferences on Cell Proliferation 9*:131-143, Cold Spring Harbor Laboratory Press, United States (1982).

Yandava, B.D., et al., ""Global" Cell Replacement is Feasible via Neural Stem Cell Transplantation: Evidence from the Dysmyelinated *shiverer* Mouse Brain," *Proc. Nat'l. Acad. Sci. USA 96*:7029-7034, National Academy of Sciences, United States (1999).

Zecchinelli, A., et al., "Epidermal Growth Factor (EGF) Enhances, in Rats, Dopaminergic Pathway 'In Vivo' an Immunohistochemical Study," *Society for Neuroscience Abstracts 16*:999, Abstract 413.17, Society for Neuroscience, United States (1990).

Zhang, S.-C., et al., "Adult Brain Retains the Potential to Generate Oligodendroglial Progenitors with Extensive Myelination Capacity," *Proc. Nat'l. Acad. Sci. USA 96*:4089-4094, National Academy of Sciences, United States (1999).

Zigova, T. and Sanberg, P.R., "The Rising Star of Neural Stem Cell Research," *Nature Biotechnology 16*:1007-1008, Nature Publishing Group, England (1998).

European Search Report for EP Application No. EP 03 00 7791, The Hague, The Netherlands, mailed Jul. 17, 2003, 5 pages.

Mignone, J.L., et al., "Neural Stem and Progenitor Cells in Nestin-GFP Transgenic Mice," *J. Comp. Neurol. 469*:311-324, Wiley-Liss, Inc., England.

Shen, Q., et al., "Endothelial Cells Stimulate Self-Renewal and Expand Neurogenesis of Neural Stem Cells," *Science 304*:1338-1340, American Association for the Advancement of Science, United States (2004).

Ying, Q.-L. and Smith, A.G., "Defined Conditions for Neural Commitment and Differentiation," *Methods in Enzymology 365*:327-341, Elsevier Inc., Netherlands (2003).

Espacenet English language Abstract of Japanese Patent Application Publication No. 2002-34580, published Feb. 5, 2002.

* cited by examiner

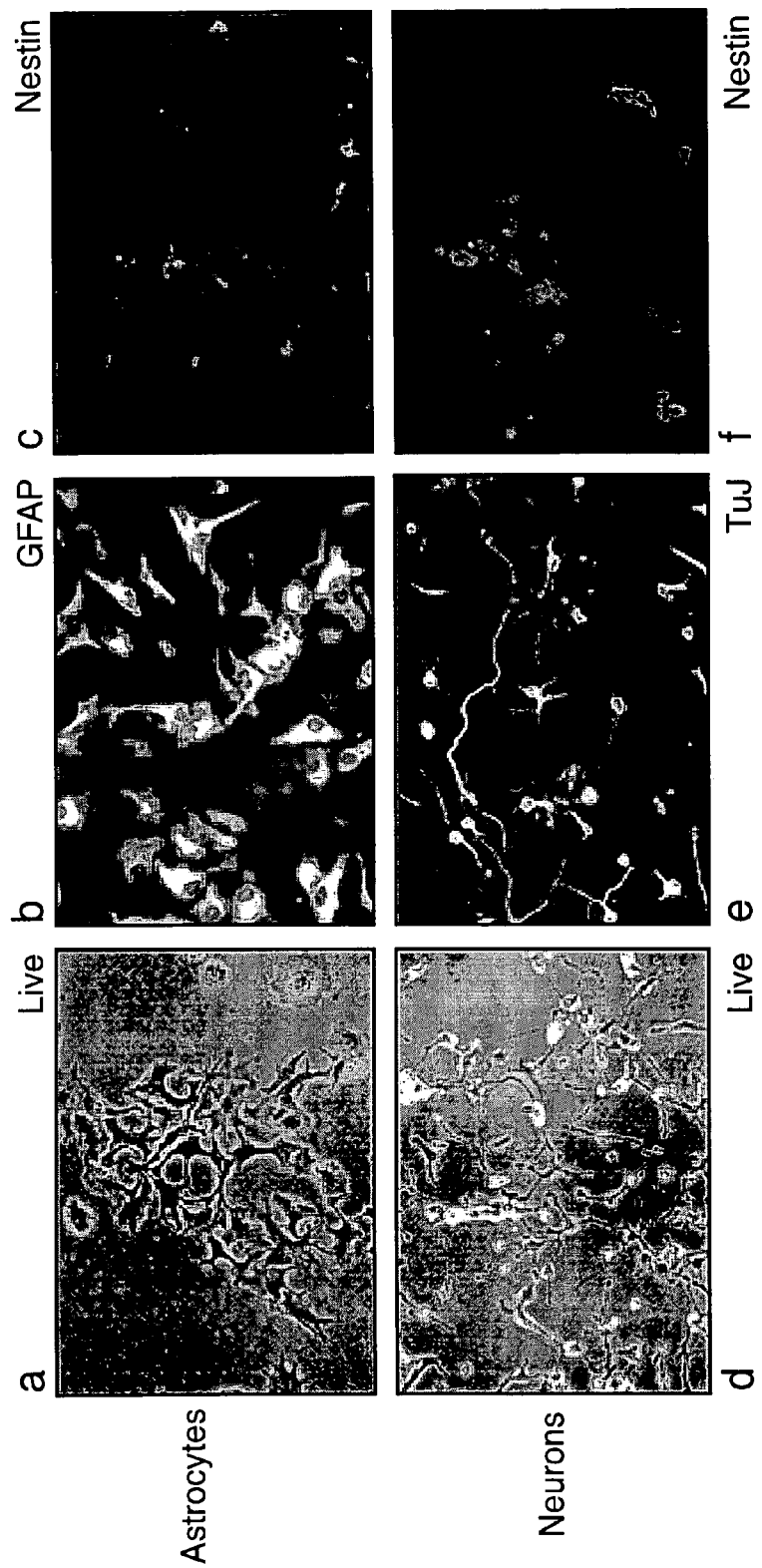

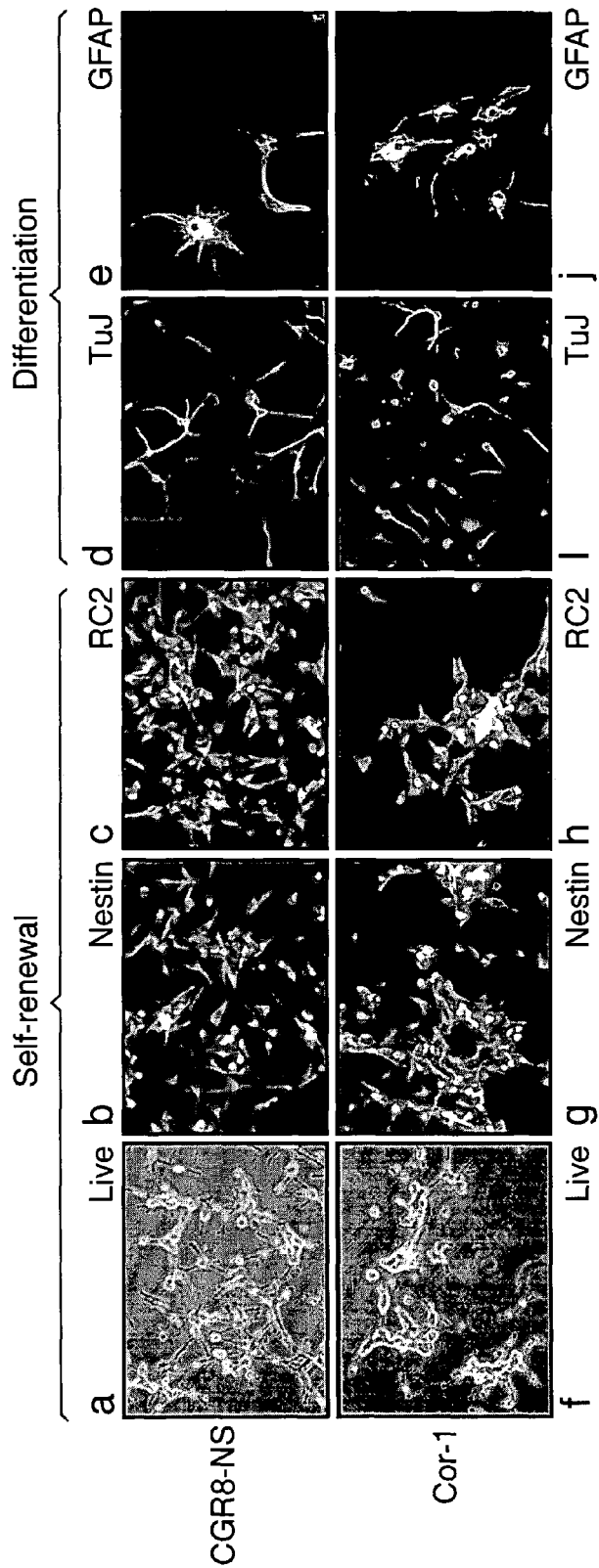

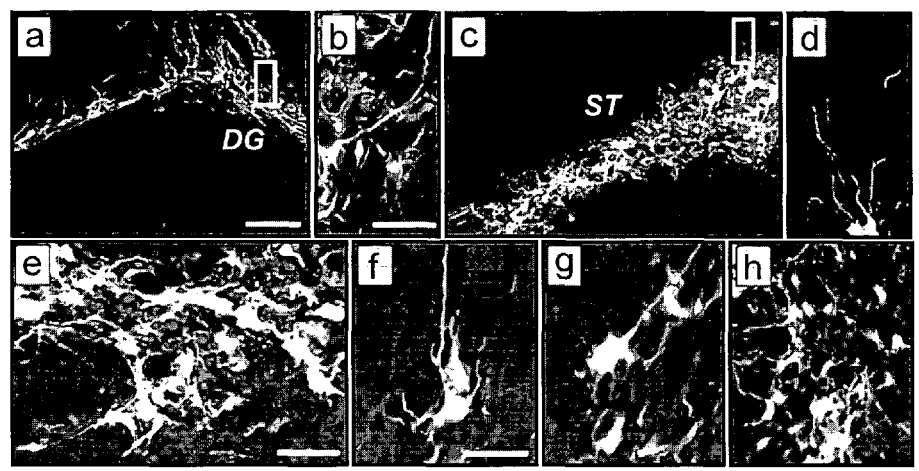
*FIG. 3*
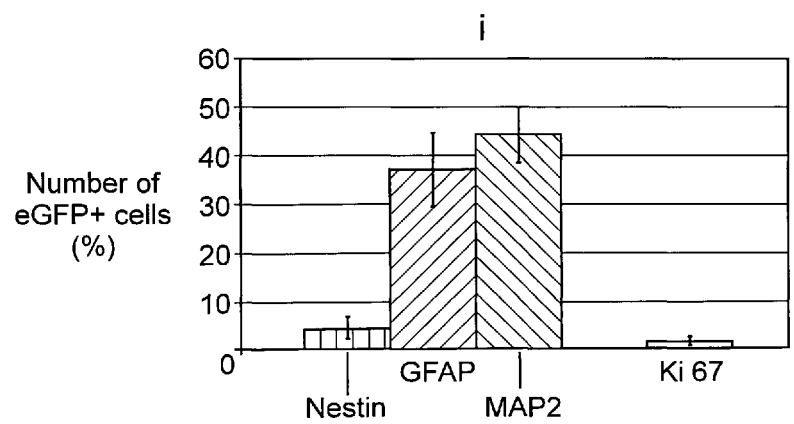

a b c 100 pA 5 msec

NEURAL STEM CELLS

The present invention relates to neural stem cells and to culture conditions and methods of culturing neural stem cells (NS cells or NSCs) in order to promote symmetrical division and self renewal of the stem cells. Compositions, cell populations, cell lines and single neural stem cells are also provided.

While neural stem cells have been purported to be isolated in vitro from a variety of sources it has not, to date, been possible to expand the cells in large-scale culture in a symmetrically-dividing, undifferentiated state. The long-term expansion of the cells in this state would be highly desirable, both from an experimental and therapeutic point of view. Having pure neural stem cell populations would enable directed differentiation into the three cell types of neurons, astrocytes and oligodendrocytes.

One known method of culturing neural stem cells, albeit as a minor component in a heterogeneous population of cells, is the neurosphere system. This system involves the serial passaging of aggregates of heterogeneous cells, of which only a tiny fraction are true neural stem cells. The majority of cells in neurospheres are committed progenitors.

There are many reports of the heterogeneity and instability of neurospheres, and their limited capacity to generate neurons (e.g. Morshead et al., 2002). Rappa et al. Neuroscience 2003 report a method for transfecting neurosphere cells by plating them on fibronectin for 1-7 days then reforming neurospheres but provides no significant characterization of the stem cells, if any, within neurospheres.

Suslov et al 2002. provide clear data that the neurosphere system is too heterogeneous to enable meaningful characterization of any stem cells within. The major conclusions are that not only is there heterogeneity within neurospheres—"that exhibit intra-clonal neural cell-lineage diversity i.e. they contain, in addition to NSCs, neuronal and glial progenitors in different states of differentiation"—but also that large differences exist in gene expression profiles between different clonal neurosphere lines. Suslov's gene expression profiling does not constitute a definition of stem cells within neurospheres as explicitly confirmed in the paper:—"the molecular phenotypes that were obtained indicate that clonogenic NSCs in our system are heterogeneous, with subsets reflecting distinct neural developmental commitments".

Much literature in this field describes the properties of glial cells. Skogh et al. MCN 2001 describe cultures of glial cells that express GFAP and stain variably for RC2 and nestin—note that mouse GFAP is not expressed in radial glia in vivo (Rakic, 2003). They report that their cells do not express Pax6, the hallmark of neurogenic radial glia (Malatesta et al., 2001, 2003), and they examine no other radial glia markers. They had heterogeneous cultures and carried out no clonal analyses.

Other accounts of radial glia in vitro consider them as differentiation intermediates or terminal products. Thus Bibel et al (*Nat Neurosci,* 2004) report the generation of neurons from ES cells via a transient radial glia-like cell, and Gregg and Weiss (*J Neurosci,* 23: 11587-601, 2003; U.S. patent publication 2003/0032181) describe "differentiation" of neurosphere cells into radial glia. Hartfuss et al (*Dev Biol,* 2001) show that radial glia are present in neurospheres.

Gregg and Weiss found that radial glia are differentiation products of neurospheres, concluding that "These results suggest that neural stem cells can give rise to RGCs [radial glia cells] and that RGC-guided migration can be recapitulated in the adult CNS". The prevailing view is that radial glia are one of the differentiated cell types arising from neurospheres.

Liour and Yu (*Glia,* 2003) show that radial glia cell differentiation can be obtained from ES cells, but as with other reports in this field do not report expansion of neurogenic radial glia.

Gobbel et al. Brain Res 2003 report propagation of multipotent rat cells "as spherical clusters of cells that grew loosely attached to the substrate", i.e. not as uniform monolayers. Further, the abstract of this paper concludes "these cells produce post-mitotic cells in approximately two of three divisions, thus making expansion difficult". There is extensive gliogenic differentiation in their cultures, but the authors find "relatively few" (<3%) neurons. They provide no molecular phenotype of their cells.

WO 01/30981 describes cultures of cells that can differentiate into neurons. But these cells are positive for GFAP and nestin, are described as astroglial cells and are a relatively impure, mixed population.

The concept that stem cells require specific cellular microenvironments, or niches, is an orthodoxy in stem cell biology. It is known, though not always acknowledged, that in neurospheres stem cells constitute only a small fraction of the total cells amongst progenitors, blast cells and immature differentiated progeny. This aggregation of mixed cell types may constitute a niche for the small proportion of cells within that may be stem cells.

There are no reports in the literature of deriving homogenous populations of neural stem cells from ES cells, only of deriving neuroepithelial precursor cells that may be expanded transiently before becoming glial-restricted (e.g. Brustle et al., Science 1999).

Hence a number of problems exist in the art.

All reports acknowledge that their cultures are heterogeneous. It has not been possible to use the neurosphere system to maintain large scale cultures of neural stem cells in a symmetrically-dividing and undifferentiated state. Other attempts to culture large numbers of neural stem cells have not succeeded beyond 5-20 passages, and have also been hindered by a high tendency of the cells to differentiate. An exception is work on adult rat hippocampal stem cells, but these are karyotypically abnormal and form neurons at low efficiency.

Whilst transient neural developmental precursors are known, permanent or near-permanent self-renewing stem cells have not been isolated and purified.

It is desired to derive neural stem cells from ES cells, and then maintain these neural stem cells in pure cultures, but this is hitherto not possible. It is also desired to derive neural stem cells from ES cells for transplantation but the persistence of ES and other non-neural cells in known ES-derived cell populations gives rise to tumours in recipient animals. It is further desired to obtain pure neural stem populations from foetal and post-natal CNS.

A complete understanding of the molecular and cellular events controlling the behaviour of neural stem cells is essential, not only as a route for understanding embryogenesis, but also as a framework upon which neural stem cells can be isolated, expanded and controlled for future therapeutic applications. The culturing methods for neural stem cells known in the art are, for reasons described above, unsuitable for use in such investigations and therapeutic applications. It is therefore desirable to develop methods and conditions for culturing large quantities of neural stem cells that allow the cells to be maintained in a symmetrically-dividing, self-renewing state. It is particularly desirable to have defined culture media, which meet the above requirements as the use of defined media is highly desirable in a clinical setting.

The present invention solves one or more of the above-mentioned problems.

In more detail, the present invention provides a method of promoting the symmetrical division of neural stem (NS) cells, comprising culturing said cells in a medium containing:—
(a) an activator of a signalling pathway downstream from a receptor of the EGF family; and
(b) an activator of a signalling pathway downstream from an FGF receptor.

In preferred embodiments, cells are cultured in the absence of serum, e.g. in medium that is free of serum and free of serum extract. It is further preferred that cells are cultured attached to a substrate, otherwise referred to as in an adherent culture. It is also preferred that culture medium contains insulin or another agonist of an insulin receptor on the cells.

In the context of the invention, it will be appreciated that the term "promoting" includes the maintenance of the neural stem cells in a symmetrically-dividing state.

According to another aspect of the present invention there is provided culture media that supports and preferably promotes the self-renewal and symmetrical division of neural stem cells in an undifferentiated state for many passages. The media substantially prevents the asymmetrical division and differentiation of neural stem cells.

The invention further provides methods of obtaining neural stem cells, and specifically as set out in the protocols herein, and additionally provides cells obtained by such methods.

The invention also provides neural cell populations, compositions, cell lines, clonogenic cell lines, and single neural stem cells, which comprise self-renewing, symmetrically-dividing neural stem cells.

Further aspects of the invention provide methods for promoting the differentiation of ES cells to neural stem cells, and methods for maintaining the neural stem cells obtained in a self-renewing, symmetrically-dividing, substantially undifferentiated state.

DEFINITION SECTION

"Neural Stem Cells"

The term "neural stem cell", as used in the present specification, describes a cell that is capable of undergoing greater than 20-30 cell divisions whilst maintaining the potency to generate both neurons and glia. Preferably, said cells are capable of undergoing greater than 40, more preferably greater than 50, most preferably unlimited such cell divisions.

Neural stem cells are capable of dividing either symmetrically, or asymmetrically. When dividing symmetrically, the neural stem cell divides to form two daughter neural stem cells or two committed progenitors, though unless otherwise specified symmetrical division refers herein to symmetrical self renewal; when dividing asymmetrically, the neural stem cell divides to form one daughter neural stem cell, and one committed progenitor (e.g. either a neuron or a glial progenitor).

Neural stem cells of the present invention can be described as radial glia, and have been shown to express at least one (and preferably all) of the radial glia markers RC2, 3CB2, GLAST, BLBP and Pax6. Preferably, the neural stem cells of the invention express RC2, 3CB2 and GLAST. More preferably, the cells express RC2, 3CB2, GLAST, and at least one of BLBP or Pax-6. Neural stem cells of the invention can also be characterized in that they are positive for the expression of at least one (preferably all) of the neural precursor markers nestin or vimentin, the LewisX antigen, Musashi-1 or prominin, and negative for the expression of at least one (preferably both) of Oct-4 or Nanog (see also Example 1-3).

The neural stem cells of the invention are by definition multipotent, i.e. they are capable of differentiating into a number of neural cell types (e.g. neurons/glia). Examples below confirm that neural stem cells cultured according to the methods of the invention retain their potency and are able to differentiate into all expected cell types.

"Sources of Neural Stem Cells"

It is possible to derive neural stem cells of the invention from a wide variety of sources. For example, neural stem cells can be derived directly from embryos, from adult tissue, from foetal tissue, or from embryonic stem (ES) cells (either wild-type or genetically modified ES cells). Preferably, the neural stem cells of the invention are derived from mouse or human ES cells, or are derived from mouse or human foetal cells.

Neural stem cells of the invention can be derived from, interalia, humans, primates, rodents, and birds. Preferably, the neural stem cells are derived from mammals, especially mice, rats and humans.

"EGF Receptor Family"

The term "EGF receptor family", as used in the present specification, describes a family of receptors (usually homodimeric or heterodimeric receptors) which can be activated by a family of EGF signalling factors. The receptors are made up of a family of four highly homologous transmembrane glycoproteins: ErbB-1 (also known as EGF-R), ErbB-2, ErbB-3 and ErbB-4.

Reference to an "EGF receptor" includes any monomeric or dimeric receptor complex of the EGF receptor family.

Each receptor has an extracellular ligand binding domain, a single hydrophobic membrane-spanning domain and a cytoplasmic tyrosine kinase domain that is responsible for signal transduction through Type-1 receptor tyrosine kinase activity. Ligand binding to any of the receptors results in receptor dimerisation and autophosphorylation, followed by phosphorylation of a number of cellular substrates leading to an array of biological effects. The receptor dimerisation may be triggered by various stimuli, including receptor ligands and toxic environmental stimuli such as UV radiation. Each dimeric receptor initiates a distinct signalling pathway by recruiting different SH2-containing effector proteins. For example, the EGF-R dimer can complex with the adaptor protein Grb, coupled to a guanine nucleotide releasing factor, SOS. The Grb-SOS complex can either bind directly to phosphotyrosine sites in the receptor, or indirectly through Shc. These protein interactions bring SOS in close proximity to Ras, allowing for Ras activation. This subsequently activates the ERK and JNK signalling pathway that in turn activate transcription factors, such as c-fos, AP-1 and Elk-1, that regulate gene expression. The EGF receptors can also activate the PLCγ signalling pathway.

"FGF Receptor"

The term "FGF receptor", as used in the present specification, describes any member of the family of transmembrane FGF receptor tyrosine kinases. There are four main isotypes of these receptors, FGFR1, 2, 3 and 4, and they are known to act in close association with the heparin and heparan sulphate (HS) systems. Reference to an FGF receptor includes any monomeric or dimeric (homo or heterodimer) complex of the FGF receptor family.

Cellular signalling pathways associated with FGF receptors include the MAP kinase pathway, and the PLCγ pathway.

"Culture Media"

Culture media used in the present invention preferably comprise a basal medium, optionally supplemented with additional components.

Basal medium is a medium that supplies essential sources of carbon and/or vitamins and/or minerals for the neural stem cells. The basal medium is generally free of protein and incapable on its own of supporting self-renewal/symmetrical division of neural stem cells.

Preferably, culture media used in the invention do not contain any components which are undefined (e.g. serum and/or feeder cells), that is to say components whose content is unknown or which may contain undefined or varying factors that are unspecified. An advantage of using fully defined media, free of serum and free of serum extracts, is that efficient and consistent protocols for culture and subsequent manipulation of neural stem cells can be derived.

"Culture Surfaces"

Typical surfaces for culture of the neural stem cells in all aspects of the invention are culture surfaces recognized in this field as useful for cell culture, and these include surfaces of plastics, metal, composites, though commonly a surface such as a plastic tissue culture plate, widely commercially available, is used. Such plates are often a few centimeters in diameter. For scale up, this type of plate can be used at much larger diameters and many repeat plate units used.

The culture surface may further comprise a cell adhesion protein, usually coated onto the surface. Receptors or other molecules present on the stem cells bind to the protein or other cell culture substrate and this promotes adhesion to the surface and promotes growth. Gelatin coated plates are particularly preferred.

The present invention is based on the observation that culturing neural stem cells attached to substrates in media comprising agonists of the EGF receptor, or agonists of both the EGF and FGF-2 receptors, promotes the unlimited, symmetrical division of the stem cells, and substantially prevents their differentiation into neurons/glia.

The various aspects of the invention are now discussed in detail.

A first aspect of the invention provides a method of promoting the symmetrical division of neural stem (NS) cells, comprising culturing said cells in a medium containing:—
  (a) an activator of a signalling pathway downstream from a receptor of the EGF family; and
  (b) an activator of a signalling pathway downstream from an FGF receptor.

Another method of the invention, for obtaining neural stem cells comprises:—
  (1) obtaining a mixed population of cells containing a neural stem cell;
  (2) replating the cells in medium comprising (a) an activator of a signalling pathway downstream from a receptor of the EGF family; and (b) an activator of a signalling pathway downstream from an FGF receptor;
  (3) culturing the cells;
  (4) harvesting aggregates of cells;
  (5) replating the cells in medium comprising (a) an activator of a signalling pathway downstream from a receptor of the EGF family; and (b) an activator of a signalling pathway downstream from an FGF receptor;
  (6) culturing the cells;
  (7) replating cells as single cells in medium containing (a) an activator of a signalling pathway downstream from a receptor of the EGF family; and (b) an activator of a signalling pathway downstream from an FGF receptor.

The method can be supplemented by selecting for cells that express a neural stem cell specific marker, for example by linking expression of such a marker to a promoter preferentially active in neural stem cells compared to its expression in differentiated progeny thereof. Preferably the method comprises passaging the cells at or below 65% confluence, more preferably at or below 55% confluence, especially below 50% confluence.

Other preferred features of methods of the invention are as set out in the protocols of the invention in Example 9.

The cultures of the invention are preferably adherent cultures, i.e. the cells are attached to a substrate.

The substrate is typically a surface in a culture vessel or another physical support, e.g. a culture dish, a flask, a bead or other carrier. Preferably, the substrate is coated to improve adhesion of the cells and suitable coatings include laminin, poly-lysine, poly-ornithine and gelatin. It is also preferred that the cells are grown in a monolayer culture and not in suspension and not as balls or clusters of cells. At higher densities, cells may begin to pile up on each other, but the cultures are essentially monolayers or begin as monolayers, attached to the substrate.

One or more signaling pathways downstream from a receptor of the EGF family can preferably be activated using an agonist of a receptor of the EGF family. An agonist of a receptor of the EGF family is suitably a member of the EGF family of signaling factors, and preferably binds to the extra cellular domain of the EGF receptor. The term "agonist" also embraces mimetics, fusion proteins, antibodies to or chimeras of the EGF family of signalling factors, and fragments, variants and derivatives thereof, capable of activating receptors of the EGF family.

The molecules that make up the EGF family of signalling factors can be characterized in that they contain at least one EGF-like domain. This domain can be defined by 6 cysteine residues that generate three peptide loops through the formation of disulphide bonds.

Specific agonists capable of acting through receptors of the EGF receptor family, and thus of activating pathways downstream of these receptors, include EGF, TGF-α, amphiregulin, heparin binding-EGF, epiregulin, betacellulin, neuregulins 1-4, and Cripto-1. Preferably, the agonist is EGF itself.

One or more signalling pathways downstream from a receptor of FGF can preferably be activated using an agonist of a receptor of FGF. An agonist of a receptor of FGF is suitably a member of the FGF family of signalling factors. The term "agonist" is also intended to embrace mimetics, fusion proteins, antibodies to or chimeras of the FGF family of signalling factors, and fragments, variants and derivatives thereof, capable of activating receptors of FGF.

Preferably, the agonist of the FGF receptor is FGF-2, or laminin-FGF.

It will be appreciated that activation of a signalling pathway downstream of a receptor of either the EGF receptor family or of an FGF receptor can also be effected by constitutively active receptors, or by downstream effectors (e.g. MEK or Bcl2) of the respective signal transduction pathways. In a particularly preferred embodiment of the invention, the signalling pathways are activated by cell-permeable small molecules, which can bypass the respective receptors and activate the signalling pathways directly. Thus, in the present invention, the term "activator" embraces all molecules capable of activating a signalling pathway downstream of receptors of the EGF family of receptors, or of an FGF receptor.

The effectiveness of the activators in the maintenance of neural stem cell cultures of the present invention is demonstrated in Examples 1-1 and 1-2 below. Here, bulk and clonal populations of neural stem cells are maintained in media comprising EGF and FGF-2 and may be passaged many times. Moreover, there is negligible/no differentiation of the neural stem cells, as is shown by the ubiquitous presence of the neural stem cell markers in the cell populations tested (see Example 1-3), and they retain their potency and are able to differentiate into all expected cell types (see Example 1-4).

Thus, the invention provides an efficient method of maintaining large populations of neural stem cells, in a self-renewing, symmetrically-dividing, undifferentiated state. Compositions of the invention include compositions comprising neural stem cells, wherein the neural stem cells are in an adherent culture and at least 50%, 70% or 80% of the cells in the composition are neural stem cells. The proportion of neural stem cells is further preferably at least 90%, more preferably at least 95%, very preferably at least 97%. Further, neural stem cells of the invention can be passaged extensively. It is preferred that the neural stem cells have been passaged at least 30 times, more preferably at least 60 times, very preferably at least 90 times. Still further, in a population of neural cells of the invention at least 80%, preferably at least 90%, more preferably at least 95%, of said cells are symmetrically-dividing neural stem cells. The cells in this compostion can be further characterized by any and all features of the invention, alone or in combination Also provided are compositions, which comprise:
neural stem cells;
an activator of a signalling pathway downstream from a receptor of the EGF family; and
an activator of a signalling pathway downstream from an FGF receptor.

The compositions preferably comprise a basal medium. It is also preferable that at least 80%, preferably 90%, more preferably 95% of the neural stem cells in the composition are symmetrically-dividing neural stem cells.

In both the neural cell populations and compositions described above, the neural stem cells are preferably free from exogenous genetic material encoding an oncogene, i.e. that they have not been subjected to immortalisation strategies. In specific embodiments, the neural stem cells of the populations/compositions are characterized in that they are positive for the expression of at least one of:
the neural precursor markers nestin or vimentin;
Sox-2;
the radial glia cell specific markers RC2, 3CB2, GLAST, BLBP or Pax-6;
the LewisX antigen;
Musashi-1; and
Prominin;
and are negative for the expression of at least one of:
Oct4, and
Nanog.

Preferably, the cells are positive for the expression of RC2, 3CB2 and GLAST. In other embodiments, (optionally in addition to the preceding marker profile) the cells are positive for the expression of at least one of BLBP, Pax-6, the neural precursor markers nestin or vimentin, the LewisX antigen, Musashi-1 or prominin. In particularly preferred embodiments (and optionally in addition to the preceding marker profiles) the cells are negative for the expression of at least one of Oct4 or Nanog.

In further embodiments (optionally in addition to the above marker profiles), the cells are positive for the expression of Sox-2, and negative for the expression of Sox-1. In certain compositions/populations comprising mouse-derived NS cells, no more than 1% of the cells are positive for the expression of GFAP or βIII tubulin, thereby confirming that there is negligible differentiation of the cells to astrocytes or neurons. In other compositions/populations, no more than 1% of the cells are positive for the expression of markers for mature astrocytes, neurons or oligodendrocytes.

The invention has also been carried out with rat cells. Thus, we have taken cells from the rat CNS and using the methods of the invention obtained a culture of rat neural stem cells having the properties of (i) high purity, typically in excess of 80% or 90% rat neural stem cells, and (ii) being cells a high proportion (a minimum of 50%) of which after many doublings, in excess of 50, in excess of 100, even in excess of 200 doublings, retained the ability to form neurons and glia. In the art cells from the rat were clearly highly heterogenous and only from the adult hippocampus. We have not obtained cells from this source, but instead from rat CNS. It is notable in this respect that the method of the invention has worked across all three species—rat, mouse, human. It is generally seen that if a single cell will form a neural stem cell colony following the methods of the invention then neurons can be obtained from cells in that colony. This is measured for example by staining separately for (i) nuclei (i.e. staining all cells) and (ii) neurons (i.e. only neurons). By comparing the relative numbers of stained cells the proportion of cells that form neurons can be calculated, A second aspect of the invention provides a method for the preparation of a neural stem cell, comprising (i) culturing neural stem cells according to the methods described above, thereby obtaining a culture of neural stem cells, and (ii) isolating a neural stem cell from said culture. Preferably, the isolated neural stem cell is one that has been conditioned to divide in a symmetrical manner.

A number of sources of cells can be used from which to derive neural stem cells. In one method, cells are obtained from nervous tissue of an animal and cultured according to the invention, to obtain a culture of symmetrically dividing neural stem cells. The nervous tissue can be from adult or foetal tissue. The nervous tissue can be from CNS, and symmetrically dividing populations of neural stem cells can be obtained from extracts taken from both adult and foetal CNS, from both human and mouse. The nervous tissue preferably comprises cells identified as having a radial glial phenotype, for example cells having this phenotype have been identified in extracts from the cerebellum and retina, both of which represent suitable further sources of cells. Neural stem cells can be obtained from diseased nervous tissue, useful for modeling disease, e.g. cells can be obtained from brain tumours for this purpose.

An option is to use the invention to derive neural stem cells from a diseased individual then (i) use those cells for assays, or (ii) carry out genetic modification prior to transplantation of cells back into that individual. Cells may thus be obtained from an individual with a neurodegenerative disorder, examples including Alzheimer's and Parkinson's diseases; or with a brain tumour.

Another method of obtaining a neural stem cell comprises:
(i) obtaining a multipotent or pluripotent stem cell capable of differentiating into a neural stem cell,
(ii) culturing the cell of (i) in medium which is non-permissive for pluripotent cells and in the presence of (a) an agonist of a signalling pathway downstream of a receptor of the EGF family and (b) an agonist of a signalling pathway downstream of a receptor of the FGF family.

In use, potentially contaminating ES cells are removed by this method, or at least substantially reduced in number, giving a purer culture and one less likely to give rise on transplantation to teratomas.

The stem cell is suitably a pluripotent stem cell, especially an ES or EG cell. The method preferably comprises culturing the cell in the presence of an agonist of the EGF receptor and an agonist of the FGF receptor.

Using NS cells of the invention, we have obtained astrocytes by removing EGF and FGF and adding serum or BMP4, we have obtained neurons by taking away EGF, then taking away FGF after an interval of about a week and plating the cells on laminin and we have obtained oligodendrocytes by taking away both EGF and FGF. Generally, all methods of the invention used to generate a neural stem cell optionally comprise a further step of differentiating the neural stem cell into a neuron, an astrocyte or an oligodendrocyte, and then further optionally using the neuron, astrocyte or oligodendrocyte e.g. in an assay, for transplantation or otherwise.

Once a neural stem cell culture has been isolated, it can then be used to establish a neural stem cell line. The establishment of such a cell line preferably includes the steps of:—
(a) obtaining a single neural stem cell,
(b) culturing the neural stem cell according to any of the methods described previously,
and thereby obtaining a clonal population of neural stem cells.

In specific embodiments, the single neural stem cell used to establish the cell line is a symmetrically-dividing neural stem cell, or a neural stem cell that has been conditioned to divide in a symmetrical manner. Preferably, the single neural stem cell is obtained according to the method described above for preparing a neural stem cell.

In preferred embodiments, the neural stem cell line obtained by the above method is a clonal population of neural stem cells, i.e. wherein all the cells are progeny of a single neural stem cell.

Single neural stem cells and cell lines (optionally obtainable by the methods described above) also form part of the invention. In a first embodiment, cell lines are provided wherein the cells are maintained in the presence of an activator of a signalling pathway downstream of a receptor of the EGF receptor family, and an activator of a signalling pathway downstream of an FGF receptor. In other embodiments, the single neural stem cells and the cells of the cell lines are characterized in that they are positive for the expression of at least one of:
the neural precursor markers nestin or vimentin;
Sox-2;
the radial cell specific markers RC2, 3CB2, GLAST, BLBP or Pax-6;
the LewisX antigen;
Musashi-1; and
Prominin;
and they are negative for the expression of at least one of:
Oct4, and
Nanog.

Preferably, the cells are positive for the expression of RC2, 3CB2 and GLAST. In other embodiments, (optionally in addition to the preceding marker profile) the cells are positive for the expression of at least one of BLBP, Pax-6, the neural precursor markers nestin or vimentin, the LewisX antigen, Musashi-1 or prominin. In particularly preferred embodiments, (and optionally in addition to the preceding marker profiles) the cells are negative for the expression of at least one of Oct4 or Nanog.

In other specific embodiments (optionally in addition to the above marker profiles), the cells are positive for the expression of Sox-2, and negative for the expression of Sox-1. In certain mouse-derived cell lines, no more than 1% of the cells are positive for the expression of GFAP or β III tubulin. In other (e.g. human) cell lines, no more than 1% of the cells are positive for the expression of markers for mature astrocytes, neurons or oligodendrocytes.

It is preferable that both the single neural stem cells, and the cells of the cell lines, are free from exogenous genetic material encoding an oncogene, i.e. that they have not been subjected to immortalisation strategies. It is also preferable that the cell lines described are neural stem cell lines.

In a third aspect, the invention provides a method of obtaining and maintaining a transfected population of symmetrically-dividing neural stem cells, comprising:
(a) transfecting ES cells with a construct encoding a selectable marker A, wherein in use said selectable marker is expressed under the control of a neural precursor cell-specific promoter;
(b) promoting the differentiation of the ES cells into neural precursor cells;
(c) selecting for neural precursor cells that express the selectable marker A; and
(d) culturing the selected cells according to any of the methods previously described.

The selectable marker A may encode antibiotic resistance, a cell surface marker or another selectable marker as described e.g. in EP-A-0695351. The neural precursor cell-specific promoter may be selected from the group consisting of Sox-1, Sox-2, Sox-3, BLBP and nestin neural enhancer. Further details of this selection strategy are provided in Example 1-1.

The neural stem cells of the invention (i.e. single neural stem cells, and neural stem cells present in the compositions, cell lines and populations of the invention) can be genetically modified. There is therefore provided a method of transfecting the neural stem cells of the invention comprising:
(a) transfecting the neural stem cells with a construct encoding a selectable marker B and a polypeptide; and
(b) selecting for neural stem cells that express the selectable marker B.

The selectable marker B may encode antibiotic resistance or a cell surface marker, and may be the same as or different from selectable marker A. Suitable transfection methods are known ones, including electroporation, lipofection, necleofection and retro- and lenti-viral transfection.

The genetically modified neural stem cells also form part of the invention, and the invention therefore provides a single neural stem cell, or neural stem cells as present in the compositions, populations or cell lines of the invention, further comprising the construct. It will be appreciated that such neural stem cells may already comprise selectable marker A, in addition to selectable marker B.

As mentioned previously, the methods of the invention are suitable for use with neural stem cells derived from any source. In one particular embodiment, the invention provides a method for obtaining neural stem cells from a source of ES cells. According to the method, differentiation of ES cells into neural stem cells is promoted by converting ES cells into neural progenitors, e.g. by culture in a monolayer or embryoid body differentiation, and then culture of neural progenitors in NSA medium. In addition, it is contemplated that the NSA medium may comprise supplemental components, such as supplemental glucose and HEPES. As an alternative, media (preferably basal media) supplemented with glucose and HEPES can also be used to promote this differentiation.

In the presence of NSA and/or glucose and HEPES, the conditions are such that the propagation of neural stem cells is favoured, with the added advantage that any non-neural cells present in the culture preferentially die. This results in a substantially pure culture of neural stem cells (e.g. at least 80%, preferably 90%, more preferably 95% of all cells present). Example 1-5 provides further details of this method.

In a preferred embodiment, the method of Example 1-5 may be used to prepare a population of symmetrically-dividing neural stem cells, which are subsequently maintained using any of the culturing methods of the invention described above.

The method of Example 1-5 can also be used to assay for the effect of factors on the differentiation of ES cells into neural stem cells. In a preferred assay embodiment, ES cells are cultured using the method described in Example 1-5, in the presence of the factor to be tested. The effect of the factor can be assessed by, for example, determining the marker profile of the resultant cells, i.e. to show whether the cells have a similar marker profile to the cells of the invention, or whether the ES marker profile is maintained. The factors tested may be either inductive or blocking factors.

There is much interest in the use of neural stem cells in the treatment of neurological and neurodegenerative diseases, and brain injuries; in particular in the treatment of diseases such as Parkinson's and Alzheimer's disease, multiple sclerosis and amyotrophic lateral sclerosis. The methods, compositions, cell populations, cell lines and single cells of the present invention are all capable of being used in such treatment, as well as in the manufacture of preparations for such treatment. Particular neurological/neurodegenerative diseases that can be treated using the invention include:—Parkinson's disease, motor neuron disease, stroke, multiple sclerosis, and Huntington's disease.

In a fifth aspect, therefore, the invention provides for the use of the cell lines, neural cell populations, single neural cells and compositions described above for cell therapy and for the manufacture of a preparation for the treatment of neurodegenerative diseases and brain injuries. Such preparations may be formulated in phosphate buffered saline (PBS).

Methods of treatment of the diseases listed above can comprise the transplantation of single cells, cell lines, compositions, or cell populations of the invention into a patient. Preferably, the patient is mammalian, more preferably the patient is human. Such transplantation has been shown to be successful in both embryonic and adult CNS and is described in more detail in Example 1-6.

The cells of the invention, and in particular the cell lines, can be used to assay the effect of inductive or blocking factors on the differentiation of neural stem cells. Such an assay may comprise contacting a neural stem cell of the invention (i.e. as present in the compositions, cell lines, and populations, or a single neural stem cell) with the factor to be tested. The effect of the factor on the differentiation of the neural stem cell can be suitably assessed by determining the marker profile of the resultant cells, i.e. to show whether the cells have a similar marker profile to the cells of the invention, or whether these markers have been lost. The cells of the invention are also suitable for assaying pharmaceuticals.

To assess the proportion of cells that will form neurons or glia, cells are propagated clonally; cells are plated individually and not all cells form clonal colonies but of those which do generally in excess of 50% will make neurons (under the appropriate protocol) or glia (again, under the appropriate protocol). The cells are distinguished from the art as while the art alleges identification of and even propagation of cells which have neural stem cell properties the populations were highly heterogenous. This is an important distinction as impure populations include cells which provide signalling to remaining neural stem cells which stimulates differentiation and further reduction of the proportion of neural stem cells. While the prior art methods can generate neurospheres from individual cells the invention enables generation of substantially pure populations from individual cells.

In particular embodiments of the invention, described in more detail in an example below, all NS cell colonies produce 15% or greater, preferably at least 20%, more preferably about 20 to 30% TuJ positive neurons. In higher density cultures we have counted TuJ positive cells. 35% of LC1 NS cells acquired neuronal morphology and expressed beta III-tubulin after 115 passages, longer than one year of continuous culture. These cells retained a diploid karyotype at this stage. LC1 is an uncloned population. Therefore the data indicate that there was minimal selective pressure for glial-restricted precursors or for genetic transformation.

Cells of the invention can be grown without co-culture with heterologous cells and without undefined conditioned media, extracellular matrix fractions or serum, a feature not previously shown for any stem cell type other than ES cells. Hence following the invention, neural stem cells are preferably grown in homogenous culture in defined conditions. Even a single NSC isolated in a microwell can expand, indicating minimal dependence on extracellular signals other than EGF and FGF and that essential extrinsic self-renewal signals for the NSCs can be reduced to EGF and FGF in vitro.

In further embodiments illustrated in an example in more detail, substantially every colony, that is at least 90%, preferably at least 95%, more preferably at least 97% of colonies that develop from plating single cells (i) show identical homogenous expression of neural precursor markers and absence of differentiation markers in FGF plus EGF, and (ii) generate neurons on growth factor withdrawal. In a specific example, every colony had these properties. This is evidence for symmetrical self-renewal. Furthermore, data from colony assays on non-cloned NS cell cultures were comparable with data from the clonal NS5 line. Serial formation of expandable undifferentiated colonies from NS5 shows that the clonogenic cells are stem cells and that their numbers expand in proportion with the NS population. Formally an increase in stem cell numbers can occur via two mechanisms: de novo generation or symmetrical self-renewal divisions. The former requires a pre-stem cell source i.e. a pluripotent cell or a foetal anlage, neither of which are present in the NS cell cultures herein, so symmetrical self-renewal must be ongoing in the NS cell cultures.

Specific NS cells, obtained in an example below, express Sox2, Pax6, Emx2, Olig1, Olig2, Nestin, BLBP, GLAST, Vimentin, and are immunoreactive for RC2, 3CB2, SSEA-1, and Prominin. Preferably they do not express Sox1 and are negative for GFAP and neuronal antigens. These NS cells lack pluripotency markers and markers of other germ layers. We contend that neural stem cell character is masked during CNS development and only truly demonstrable ex vivo, as is the case with ES cells. The finding that Sox1 expression was not maintained in the NS cells is new, unpredicted, and indicates that continuous lineage selection using Sox1 would not be productive.

In further embodiments of the invention NS cells, exemplified by ES cell-derived uncloned (CGR8-NS) and cloned (NS5) NS lines and foetal cortex-derived uncloned (Cor1) and cloned (Cor1-3) NS lines, show expression of radial glia markers 3CB2, BLBP, GLAST, Nestin, RC2 and Vimentin in culture. Expression of GFAP is preferably in fewer than 10%, more preferably fewer than 5% especially in fewer than 2% of cells in any of these cultures. In a specific example GFAP expression was seen in fewer than 1% of cells. We have also shown uniform expression of nestin and RC2 with absence of GFAP and βIII-tubulin in ES cell derived NS cells after 115 passages indicating that the NS cell phenotype is stable. Preferred cells of the invention are differentiated from ES cells and (1) continue to express nestin and RC2 and (2) continue not to express GFAP and βIII-tubulin after 30 passages, preferably after 60 passages, more preferably after 100 passages. Non-expression of GFAP and beta III-tubulin means expression is seen in fewer than 5% of cells, preferably fewer than 2% of cells.

We have carried out analysis via RT-PCR which confirmed absence of pluripotent, mesodermal, or endodermal specific transcription factors in specific NS cells. We have also carried out Affymetrix® expression profiling that confirms the absence of lineage inappropriate transcripts and demonstrates consistent expression of neural and radial glia markers in three different NS cell cultures (ES derived, foetal cortex-derived, and clonal foetal cortex-derived).

Obtaining NS cells by differentiation from ES cells preferably comprises maintaining the cells in continuous adherent culture, and more preferably omits a step of forming a neurosphere. However, obtaining NS cells by differentiation of cells from primary cell isolates from foetal or adult brain optionally comprises (i) first forming a suspension aggregate or a neurosphere, and (ii) subsequently maintaining the cells in adherent culture. We have found in examples that after a few days the aggregates can be attached to gelatin-coated plastic and NS cells will then grow out.

We determined the proportion of neurons and astrocytes generated at early and late passages of cells of the invention, specifically for the LC1 NS cells at passages 8 and 115. The latter culture represents 12 months of expansion with a doubling period of 24 hours. There is a modest decline in the number of neurons obtained at late passage, but this still totals>35%. The NS5 clonal line, independently derived from 46C ES cells, shows a similar level of neuronal differentiation efficiency at passage 30. Generation of GFAP immunoreactive astrocytes approached 100% at both time points for the LC1 NS cells and also for NS5 cells. Furthermore, the in vivo data, which show extensive differentiation of both neurons and astrocytes, were obtained using LC1 NS cells grown for multiple passages, then transduced with GFP lentivirus and expanded further before transplantation. In combination with the uniformity of radial glia marker expression, the data on stable differentiation potential for the uncloned LC1 NS cells indicate that adherent culture in FGF and EGF favours stem cell self-renewal and suppresses commitment to either glial or neuronal fates.

We found NS cells, obtained by differentiation from ES cells, could be transplanted without formation of tumours over a period of 5 weeks, thus being distinct from ES cells which would give rise to macroscopic teratomas within 4 weeks in the mouse brain.

The present invention also relates to nuclear reprogramming methods and to cells and animals obtained via those methods.

Nuclear reprogramming is a technique by which the nucleus of a somatic cell, optionally a stem cell or a terminally differentiated cell, is reprogrammed so as to behave as a nucleus of a cell of relatively higher potency; ultimately a completely reprogrammed nucleus acts as the nucleus of a pluripotent cell and reprogramming is often taken to mean reprogramming all the way to pluripotency. Methods of reprogramming by nuclear transfer are well established in the art and became well publicized after the invention described in WO 96/07732, sometimes referred to as the "Dolly the sheep" invention. Nuclear transfer can thus be used to clone non-human animals.

Nuclear transfer methods have a number of problems. Primarily they remain of low efficiency, in that the cells obtained are rarely reprogrammed so as to be truly pluripotent. It is also desirable to be able to carry out genetic manipulation on the nucleus as part of the reprogramming. But, at present this manipulation is not possible or is unreliable due to the difficulty in obtaining clonal populations of donor nuclei. Even with clonal nuclei the reprogramming methods are complex procedures that require many individual steps. Lastly, ES cells from some species remain difficult to isolate. Using reprogramming techniques, if such were available and reliable, may offer an alternative route to pluripotent cells in these species.

Further aspects of the present invention have as an object to provide alternative approaches to the above problems and to provide solutions thereto.

Accordingly, the invention provides a method of nuclear reprogramming, wherein the donor nucleus is obtained from a neural stem cell of the invention.

Neural stem cells of the invention have been found to be reprogrammable at high efficiency, and hence the invention provides an efficient reprogramming method and also facilitates production of genetically modified reprogrammed cells, especially pluripotent stem cell, of many species. The ability, via the invention, to propagate individual neural stem cells clonally means that after genetic manipulation clonal populations of cells can be obtained, all with the same genetic modification, and used in reprogramming methods.

It is also possible to identify neural stem cells according to the presence of specific cell surface markers and/or the absence of others—this has the advantage that the step of culturing according to aspects of the invention described herein can be omitted, as the neural stem cell can be picked directly from a mixed population, e.g. a brain homogenate.

A method of nuclear reprogramming is hence provided herein, wherein the donor nucleus is from a neural stem cell obtained according to any embodiment or aspect of the invention.

A particular method of nuclear reprogramming, comprises:
obtaining a donor cell;
obtaining a recipient cell;
transferring the nucleus of the donor cell into the recipient cell, wherein the donor cell is (i) a neural stem cell, or (ii) a cell obtained according to a method of the invention; and
culturing the cell so as to reprogram the donor cell nucleus, thereby obtaining a reprogrammed cell.

The nucleus of the recipient cell will generally be removed at one stage in the process so the resulting cell is diploid, this is done optionally prior to transfer of the donor cell nucleus and optionally after transfer of the donor cell nucleus.

One of the interesting possibilities offered by NS cells of the invention is to introduce genetic lesions e.g. that may induce malignancy. A further option is thus to genetically manipulate the donor cell nucleus. This can be used to introduce mutations or genes of interest, e.g. to generate cells or animals for assays or other test purposes wherein a plurality of cells are obtained all with the same manipulation. The range of manipulation is wide. One example is to introduce a disease-causing genetic sequence or a putative disease-causing genetic sequence into the donor cell nucleus, useful for drug screening. A further option is to obtain an animal comprising tissue derived from the reprogrammed cell and carry out an assay using the tissue. It is preferred that the cell is reprogrammed back to pluripotency, e.g. by nuclear transfer into an oocyte.

In particular embodiments of the invention, taking advantage of the knowledge from the invention of cell surface makers in the desired neural stem cells allows omission of cultures steps otherwise needed to isolate a neural stem cell from a mixed population. One such reprogramming method comprises providing a mixed population of cells, isolating a neural stem cell from the mixed population based upon its cell surface marker profile, and transferring the nucleus of the isolated cell to a recipient cell.

As with the other methods, the isolated cell can be genetically manipulated prior to transferring its nucleus to the recipient cell. Also, the isolated cell can be cultured to obtain a clonal population of cells prior to transfer of the nucleus of one cell in the population to the recipient cell.

In more detail, an application of the cells of the invention is in high throughput drug screening. Both neural stem cells of the invention and neurons, glia etc obtained therefrom can be used for the screening, e.g. to identify factors active on either type of cell. The cells or progeny can be used in models of brain cancer. Cells and progeny can be obtained from a tumour of the nervous system, especially the CNS and the neural cells derived therefrom and their progeny used in screens: the nature of the screen is believed to be apparent to all, but in outline comprises obtaining a cell of the invention or a differentiated progeny thereof, culturing the cell or progeny in the presence of a test factor and determining an effect of the factor on the cell or progeny. In a particular screening use, a cell is provided, which is a cell of the invention or obtained by the invention and which has been modified so as to express an EGF receptor or an additional EGF receptor.

The cells can be modified before being used in a screen. For example, the cells can be genetically modified to introduce a mutation in a gene, or to introduce a nucleic acid encoding a gene product known to be or suspected to be implicated in disease, especially a disease of neural cells including Parkinsonism and Alzheimer's. The Parkin mutation can be introduced. A gene encoding a protein, e.g. APP, implicated in Alzheimer's can be expressed or mutated or have it expression altered.

Cells of the invention are of use as a source of cells for cell therapy. They offer a source of stem cells from a patient which potentially can be a source of nuclei for nuclear transfer. They can be used for delivery of gene therapy, including neuroprotective gene therapy. In an example therapy, a cell of the invention expresses glial cell derived neurotrophic factor (GDNF). These cells can be obtained by following the invention and genetically manipulating the cells. The cells can be transplanted to restore damaged neural circuitry and/or restore brain function.

An advantage of the invention lies in the purity of the cells obtained. A pure population is easier to control in transplantation or culture, as in a heterogenous culture a reduced percentage of neurons is obtained as more cells are already committed to a glia fate. Some therapies will need both neurons and astrocytes.

Other therapies will need glial cells (e.g. oligodendrocytes for MS, astrocytes, migratory cells, for other applications).

Methods of cloning of non-human animals are provided by the invention. One method of cloning a non-human animal, comprises (i) obtaining a neural stem cell from the non-human animal, (ii) obtaining an oocyte of the same species as the non-human animal, (iii) transferring the nucleus of the neural stem cell into the oocyte, and (iv) implanting the cell obtained in (iii) into a female of the same species. The invention hence provides an efficient method of non-human animal cloning based upon isolation of neural stem cells. The cloning method is believed to be of application to substantially all non-human animals, though especially domestic animals including cows, pigs, sheep, cats, dogs, chickens and others and also laboratory animals including mice and rats.

The invention enables, for the first time, growth of a pure population of diploid, clonogenic, transfectable, tissue stem cells in the same way as ES cells. This is a significant step forward in stem cell biology that opens up a range of new experimental opportunities. For example, previous studies on profiling "neural stem cells" are seriously compromised by reliance on heterogeneous neurosphere cultures (e.g. Suslov et al.). Moreover, the radial glia characteristics of NS cells define their in vivo counterpart. The ability to culture and genetically manipulate pure populations of radial glia also opens up new opportunities for analysing the cell biology of these remarkable cells, that can function both as stem cells and as specialised scaffold cells. Finally, the ability to propagate NS cells in simple media without heterologous cells or cell extracts establishes that self-renewal can be driven by growth factors alone and does not require a complex microenvironmental niche, hitherto considered indispensable by stem cell biologists. The invention opens up new approaches to nuclear reprogramming and optional genetic manipulation using the cells.

The invention provides efficient generation of neurons from NS cells. In a method, set out in more detail in a protocol herein, a method of obtaining neurons comprises (a) culturing neural stem cells in the presence of an agonist of an FGF receptor and in the absence of an agonist of an EGF receptor; and (b) thereafter, culturing the cells in the absence of an agonist of an FGF receptor and in the absence of an agonist of an EGF receptor. It is found that the period during which e.g. EGF is absent primes the cells to become neurons when e.g. FGF is subsequently withdrawn. The neural stem cells are preferably plated in monolayer culture. Typically, the NS cells are transferred to medium free of EGF but which contains FGF-2 and cultured for a period, say at least 2 days, or at least 4 days, before FGF-2 is also removed from the medium (which includes that cells are transferred to medium that does not contain it). In a specific method the cells are grown in FGF-2 but no EGF for a week and then FGF-2 is withdrawn. Withdrawal of FGF leads to some cell death in the culture, but a good percentage survive and form neurons. This method may be used as an optional addition to any of the methods described herein for derivation of NS cells.

It will be appreciated that methods/uses according to all aspects of the invention can be carried out either in vivo or in vitro.

The methods and compositions of the invention are illustrated in the accompanying drawings in which:—

FIG. 3 shows NS cells incorporate and differentiate within the adult brain;

Figure 1A:
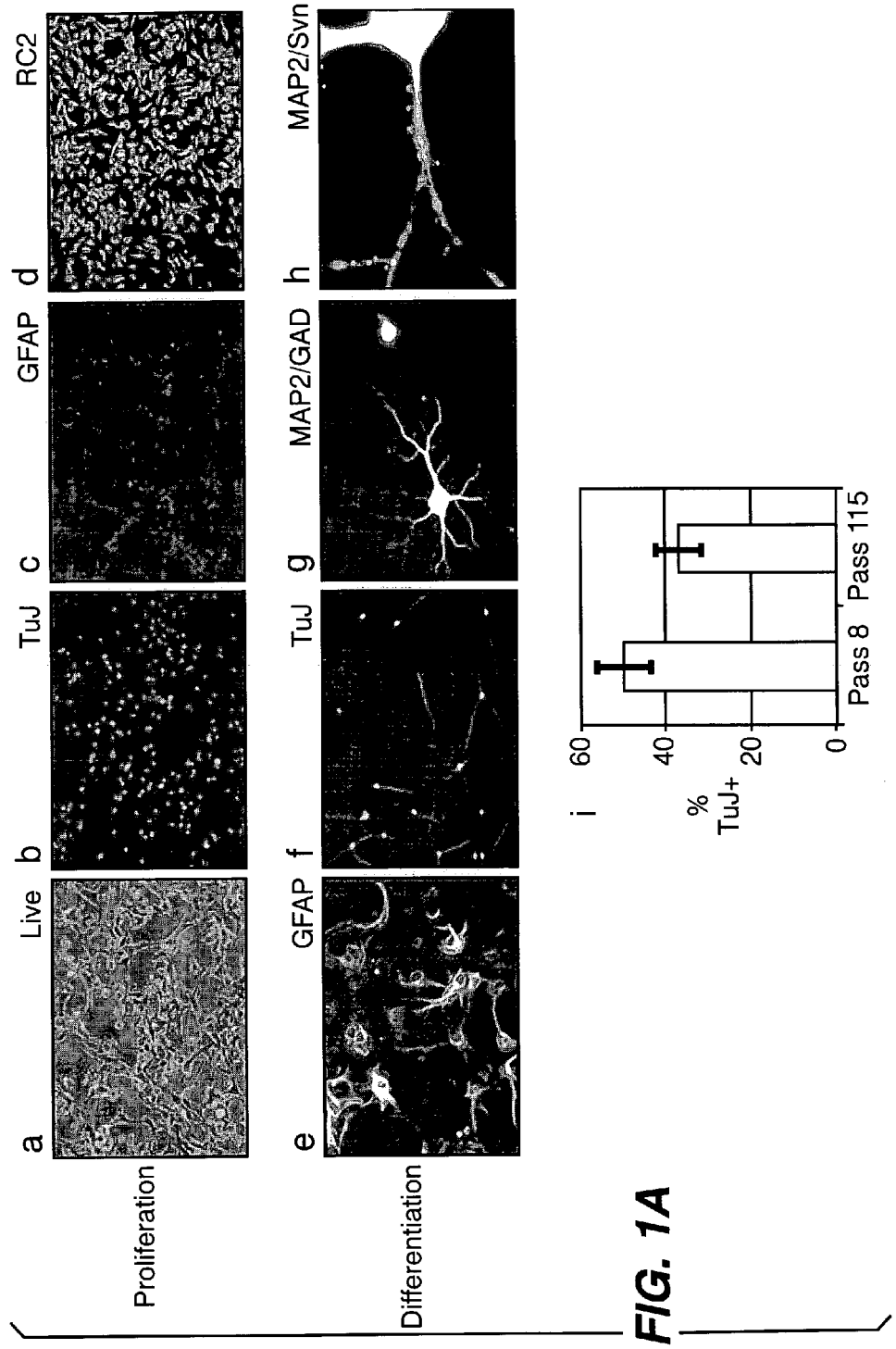
FIG. 1 shows generation of neural stem (NS) cells from ES cells.

Referring to the figures in more detail, FIG. 1 shows generation of neural stem (NS) cells from ES cells: A. The adherent NS cell culture (LC1) propagated in EGF and FGF-2 (a) shows no expression of neuronal (b) or astrocyte (c) antigens and uniform expression of the precursor marker RC2 (d) and nestin (not shown). LC1 cells differentiate into immunopositive astrocytes (e) on addition of serum and generate neurons (f-h) on growth factor withdrawal. The proportion of neurons obtained remains >35% of total cells after 115 passages (i). B, Clonal NS-5 cells were generated through Sox1 neural lineage selection. a and c, Phase image of neural precursors at passage 1 and 5 respectively. b and d corresponding Sox1-GFP fluorescence. e, Single cell 1 hour after plating in Terasaki well. f, Phase contrast image of clonal cell line at passage 20. C, RT-PCR for ES cell and neural stem cell/radial glia cell markers (46C, parent ES line; P5, 5 passages after neural differentiation; NS-5 clonal NS line; LC1, NS population (passage 17); brain, E12.5/E16.5 mouse brain). D, NS-5 immunoreactivity for neural stem cell/radial glia markers. E, NS-5 differentiation into astrocytes (a,b) and neurons (d,e) with loss of nestin immunoreactivity (c, f) F, Colonies of NS-5 cells (a) generate neurons on growth factor withdrawal (b) and in the presence of EGF/FGF retain homogenous expression of RC2 and BLBP with no immunoreactivity for GFAP (c,d). G, Metaphase spread of NS-5 (passage 31).

FIG. 2 shows NS cells can be derived from various ES cell line and foetal forebrain: NS cells were derived from independent ES cell lines (CGR8, E14Tg2a) or primary cortical (Cor-1) and striatal (Str-1) tissue. A, RT-PCR of stem cell/radial glia markers. B, RT-PCR for transcriptional regulators. C, The ES-derived line (CGR8-NS) and foetal-derived line (Cor-1) are indistinguishable from LC1 by morphology (a, f) and neural stem cell/radial glial marker immunoreactivity (b, c, g, h), and can each differentiate into neurons (d, i) and astrocytes (e, j).

Figure 4A:
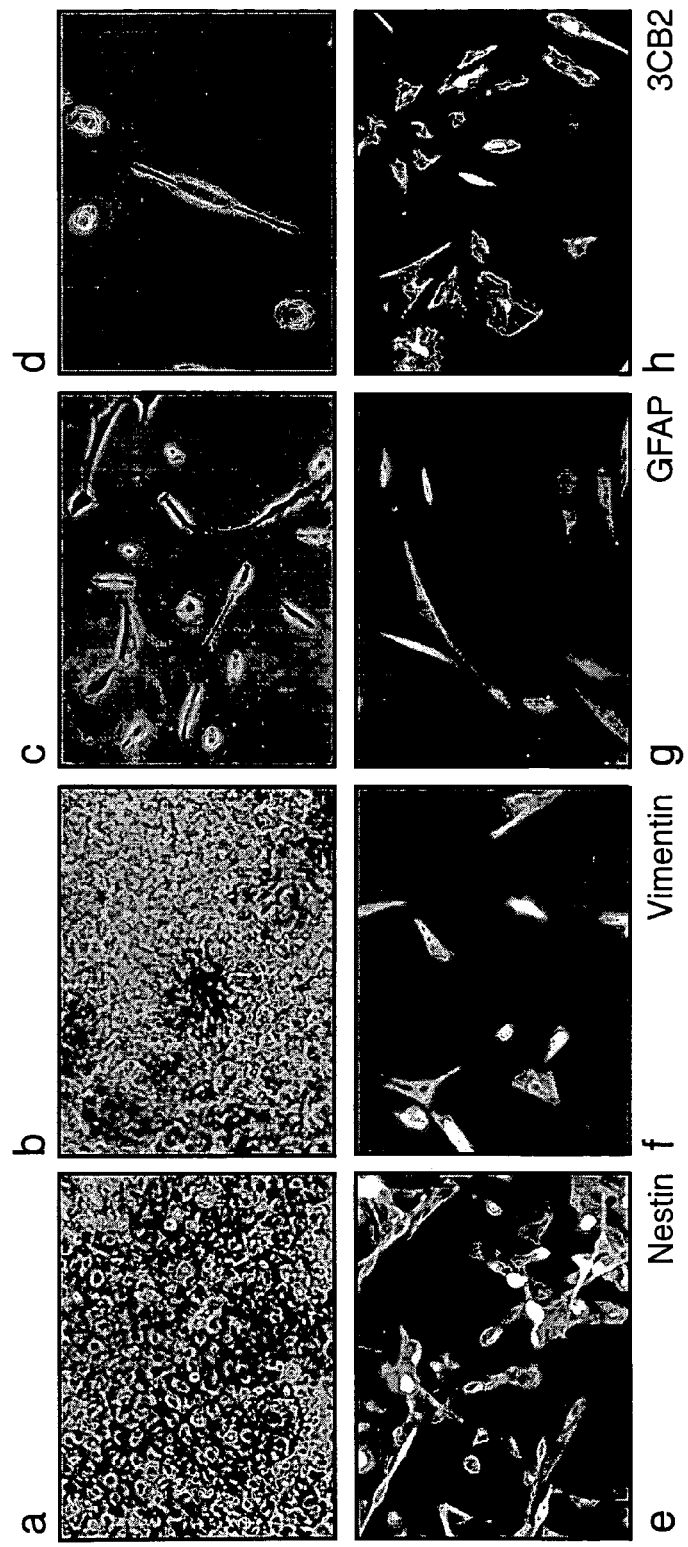
FIG. 4 shows human ES cell or foetal-derived NS cells.

FIG. 3 shows NS cells incorporate and differentiate within the adult brain: a-h, Confocal images of LC1 NS cells, lentivirally transduced with eGFP, four weeks post-grafting into hippocampus (a, b) or striatum (c-h). b, d, higher magnification of the insets in panels a and c, respectively. e, f, Examples of eGFP grafted NS cells (green) showing co-expression (yellow) of the neuronal markers TuJ (e, red) or MAP-2 (f, red). g, astroglial marker GFAP (red). h, neural progenitor marker nestin (red). i, Quantitative analysis of graft-derived neuronal (MAP2), astroglial (GFAP), progenitor (Nestin), and proliferating (Ki67) cells, four weeks after transplantation into adult mouse striatum. Data are means (±standard deviation) of at least 500 eGFP+ cells from five independent animals. Scale bars: a,c, 100 □m; b, d, e, 40 □m.; f-h, 20 □m. FIG. 4 shows human ES cell or foetal-derived NS cells: A, Derivation from human ES cells. a, human ES primary culture. b, differentiation of human ES cells into neural-rosette structures. c, passage 9 in NS expansion medium. d, individual cells exhibit radial glial morphology. e-h, immunostaining for neural stem cell/radial glia markers. B, Derivation from human foetal forebrain. i, neurospheres generated from cortex. j, attachment and outgrowth. k, passage 5 in NS expansion medium. I, radial glia morphology. m-p, neural stem cell/radial glial markers. C, Differentiation. q, TuJ positive immature neuron. r, GFAP positive astroglia.

FIG. 5 shows: A. Superimposed inward and outward current tracings obtained at different membrane potentials (between −70 and +40 mV from a holding potential of −90 mV), from three different NS cells following incubation in differentiating medium for six (a), twenty (b) and thirty days (c). B. superimposed voltage responses obtained following injection of depolarising rectangular current pulses in the same three cells (a, b and c) as in (A) by switching from voltage- to current-clamp immediately after current recordings shown in (A) were obtained. The dashed line represents a voltage level of −60 mV. C. Average Na$^+$ currents elicited at −20 mV from cells cultured in differentiating medium for increasing times as indicated by labels. Bars indicate SE. D. Superimposed inward currents elicited at −40 mV and 0 mV in 10 mM Ba$^{2+}$ and in the presence of TTX; the holding potential was −90 mV. E. Current/voltage relationship from the same cell as in (D).

The invention is demonstrated in use by the following examples.

EXAMPLES

Example 1-1

Isolation and Culture of Bulk Populations of NS Cells

An ES cell differentiation protocol was recently established that allows efficient and consistent generation of between 50-70% Sox1 positive neural precursors in adherent monolayer culture. In order to isolate, expand, and characterise the neural precursors (derived from mice) within these cultures, a previously generated cell line (46C cells) was used which contained a GFP-IRES-puromycin reporter cassette targeted to the Sox1 locus (Ying et al., 2003b). Puromycin was added to the differentiation cultures after 7 days, and within 3 days more than 95% of remaining cells were GFP+ neural precursors. At this point, cells were re-plated in N2B27 media supplemented with EGF/FGF-2 (without puromycin). These cells grew rapidly, within a few passages taking on a homogeneous morphology.

These 46C neural precursor cells (46C-NP) were kept continuously in culture for more than 20 passages retaining a characteristic bipolar morphology. These cultures showed very little cell death and had a high plating efficiency with doubling time of approximately 25 hrs.

Example 1-2

Culture of Cell Lines

To isolate clonal cell lines, single cells from passage 5 bulk cultures of 46C-NP cells were plated into separate wells of a microwell plate. Of 95 single cells scored, 15 were grown up into colonies and, of these, 4 lines were kept growing continuously through more than 10 passages. One line (NP5) showed the characteristic bipolar cells with homogenous morphology identical to that observed in the bulk population. This NP5 line has been maintained in culture indefinitely (NP5 passage 41; more than 5 months).

Example 1-3

Characterization of NS Cells

In order to characterise both the bulk cell population and clonal lines immunocytochemistry was used for a range of markers. As expected, each of the cell lines was found to be positive for the neural precursor markers, nestin or vimentin. Importantly, these cells were also positive for the radial glia specific markers RC2, 3CB2 and astrocyte-specific glutamate transporter (GLAST). Less than 1% of cells were positive for either GFAP or b III tubulin suggesting that very little spontaneous differentiation to astrocytes or neurons occurs during passage of these cells. Unlike primate/human cells, rodent radial glia are negative for GFAP. Furthermore, these cells are immunoreactive for SSEA-1, an antibody that recognises the LewisX antigen, previously used to enrich for adult neural stem cells.

RT-PCR was performed with a range of markers to confirm their identity as radial glia. All four clonal lines as well as the bulk population were negative for Oct4 or Nanog confirming that they were not ES cells, while they did express nestin, vimentin and GLAST, consistent with the immunocytochemistry. Furthermore, each cell line showed expression of BLBP, a radial glia marker. These cells also express Musashi-1 and prominin.

Interestingly, the bulk culture of 46C-NP gradually lost expression of Sox1, as assessed by the GFP reporter, such that by passage 5 (~2 weeks) very few cells remained green. Also, none of the clonal lines showed Sox1 driven GFP expression. RT-PCR confirmed that these cells did not express Sox1, but instead expressed the related SoxB1 class protein, Sox2. Taken together these results suggest that a range of Sox1 expressing neural precursors can be isolated using a puromycin selection strategy, and that Sox1–, Sox2+ cells with properties of forebrain radial glia can be isolated and clonally expanded.

Example 1-4

NS Cell Line Differentiation into Neurons and Glia

The molecular markers expressed by the NS cell lines confirm that they are a type of neural precursor cells. To confirm that these cells were true multipotent stem cells (i.e. capable of differentiation as either neurons or glia) a range of conditions designed to test the potency of the cells were tested.

Previous investigations of neural precursors induced differentiation through protocols involving withdrawal of mitogens and/or addition of serum or other cytokines. In the present case, EGF, FGF, or both, was withdrawn from proliferating NP5 and 46C-NP cells cultured on plastic. Simultaneous removal of both EGF and FGF resulted in rapid and extensive cell death within 24 hrs. Culture with FGF alone, by contrast, lead to cell death over the course of 3 days. Culture in EGF alone resulted in no cell death or differentiation, but cell proliferation was reduced. Thus, EGF clearly acts an essential cell survival signal (partially compensated by FGF signalling) for NS cells cultured on plastic.

The effect of serum on proliferating cells after withdrawal of cytokines was also tested. Cells treated in this way survived, even in the absence of EGF, and rapidly differentiated in a synchronous manner such that 100% of cells acquired a large flat astrocyte that stained positive for GFAP and negative for nestin. Therefore, all NS cells within a proliferating population are capable of differentiation as astrocytes. This effect can be mimicked by addition of BMP4 in absence of serum following EGF/FGF withdrawal on plastic. CNTF and TGF-b behaved similarly to BMP4, although the astrocyte morphology was different and there was more cell death initially. BMP, CNTF and LIF have each been shown to induce a astrocyte fate from primary cortical progenitors (Gross et al., 1996; Lillien and Raff, 1990; Nakashima et al., 1999). Consistent with these studies, a rapid induction of Id genes (>30 fold) with BMP-4 or serum treatment was found (data not shown).

In an attempt to induce neuronal differentiation, the withdrawal of EGF on laminin-treated dishes was tested. To avoid cell death seen with culture of cells on plastic, the cells were plated on a laminin substrate in the presence of FGF, but no EGF. The PCD seen in these conditions on plastic or gelatin did not occur and cells survived. There was a change in morphology of the cells to more extended bipolar processes, with characteristic endfeet of radial glia. These cells showed a drastic reduction in proliferation (through BrdU incorporation) but maintained radial glia markers (RC2, vimentin, nestin) and did not differentiate, as only a small proportion of neurons or astrocytes was seen in regions of high density. To induce neuronal differentiation, after 6 days the media was changed from NSA/N2 +FGF2 to NSA/B27 without FGF2. This promoted around 40-60% neuronal differentiation of cells as judged by MAP2 and bIII tubulin antibody staining. These neurons were GABAergic as assessed by GABA immunoreactivity, while there were few astrocytes (GFAP). These results are consistent with the previously described role of FGF in preventing neuronal differentiation.

It was also found that each cell line could be frozen and thawed with similar success to ES cells.

In further tests, the differentiations were attempted starting from single cells. This clonal expansion and differentiation showed all the cells to have ability to form neurons.

Example 1-5

Isolation of NS Cells from any ES Cell Line without Use of Genetic Selection Strategies The N2B27 media used to isolate NP5 was originally optimised for conversion of ES cells to neural precursors and hence allowed good survival of both ES cells and neural progenitors. Thus, in the absence of puromycin selection, it was not possible to efficiently expand 46C-NP cells with EGF and FGF-2 due to carry-over of ES cells and non-neural cell type (data not shown). To overcome this and allow the generation of radial glia cells from other non-targeted ES lines, other basal media combinations were tested that allowed survival and expansion of neural precursors but not other cell types.

Using a commercially available media, NS-A media (Euroclone), it was found that re-plating of a 46C ES cell monolayer differentiation at day 7 resulted in formation of clumps/spheres of cells, as well as a cell death of non-neural cells. Subsequent attachment of these cell clumps occurred and a homogeneous population of cells were outgrown. Further characterization of this passagable population (>75 passages) of cells revealed an identical profile of expressed markers seen previously using the puromycin selection strategy. Thus, the cells were positive for neural precursor markers (nestin, vimentin) and also radial glia markers (RC2, GLAST, BLBP and Pax6). 46C-NP cells behaved similarly in either N2B27 or NSA media once established with only small differences in morphology, and no differences in marker genes.

Using this protocol, cell lines from six other ES lines were isolated: CGR8, E14T, Oct4-GIP, S11, R1 and V6.5. Each of these cell lines has a similar morphology and expression profile and can be passaged extensively.

Example 1-6

Transplantation of NS Cells

To test the potential of the NS cells in vivo, they were transplanted into both embryonic, and adult CNS, as well as in kidney capsule graft.

Electroporation was tested on NP5. They were found to be electroporated efficiently using a square wave elecroporator. The cells are also transfectable using lipofectamine plus reagent. This is a major advantage as all genetic manipulations used in mouse now become available.

To allow rapid evaluation of the grafted cells, 46C-NP were transduced with lentiviral particles carrying the eGFP marker gene. The infection was highly efficient and almost 95% of the cells were successfully marked, the eGFP signal being strong and stable with passages. The use of the lentiviral infection allowed the transgene to be stably integrated and the signal to remain stable for long term analyses of the grafted cells.

The behaviour of the cells following transplantation in the embryonic brain (an environment that contains all the molecules and factors able to sustain and direct differentiation of immature neural cells) was evaluated. 100,000 cells were resuspended in a final volume of 2 microliters following the procedure previously described by Magrassi and colleague (Magrassi et al., Development 1999) using E14.5 mouse embryos as recipients. The cells survived well after transplantation (an approximative evaluation of around 20000 cells in the graft was made), the eGFP signal was easily detectable and they displayed migrational activity already at early time points after the grafting. The fates that the grafted cells acquired at different time points (4 days, 7 days, 2 weeks and 1 month) after the grafting were analysed. At the 4 day and 1 week time points, the majority of the cells were still immature as indicated by the nestin immunoreactivity, while 23% expressed the neuronal marker Tuj-1 and 16.3% acquired the glial marker GFAP. These data indicate that the transplanted NS are able to generate both neurons and glia in vivo as expected from multipotent NS cells.

The NS cells were also transplanted into the adult striatum. In these transplants, the cells survived well (the survival is anyway lower than in the embryonic grafts) and differentiated toward both neuronal and glial fates. Quantitative analyses performed at 2 weeks after transplantation indicated that 43.3% of the cells expressed the neuronal-specific marker Tuj-1, while 26.6% displayed immunoreactivity for the glial marker GFAP. A small fraction of the cells (11.1%) retained an immature phenotype as indicated by the expression of nestin.

NP5-GFP cells into kidney capsule did not give rise to teratomas (n=4, data not shown).

Example 2

Example 2-1

Methods

Mouse Cell Culture and Differentiation

ES cells and neural differentiation are detailed by Ying & Smith, 2003. NS cells termed LC1 and other ES cell-derived NS cells were routinely generated by re-plating day 7 neural differentiation monolayer cultures on uncoated plastic in NS-A medium (Euroclone) supplemented with N2 and 10 ng/ml of both EGF and FGF-2 (NS expansion medium). Cells formed aggregates which subsequently attached and outgrew NS cells. Cells termed 46C-NS cells were generated after addition of 0.5 µg/ml of puromycin to differentiating adherent cultures at day 7. Cells were re-plated 3 days later into an uncoated T75 flask in N2B27 media with 10 ng/ml of both EGF and FGF-2 (Peprotech) in the absence of puromycin. A clonal line, NS-5, was generated by plating single cells into 96-well microwell plates (Nunc) by limiting dilution (single cells scored one hour after plating). Primary cultures were generated using standard protocols from cortex/striatum of E16.5 mouse embryos and allowed to attach on flasks treated with 0.1% gelatin. Cor-1 and Str-1 cells were then expanded on gelatin using NS expansion medium. For astrocyte differentiations, NS cells were replated onto 4-well plates at $1\times10^5$ cells/well in NS-A medium supplemented with 1% fetal calf serum or 10 ng/ml BMP4 (R&D System). For neuronal differentiation $5\times10^4$ NS cells were plated into poly-ornithine/laminin treated wells in NS-A supplemented with FGF-2 alone. After 7 days the media was switched to NS-A supplemented with B27 (Gibco) without growth factor. For clonal differentiation, 1000 cells from NS-5 or Cor-1, cultures were plated in 10 cm plates pre-treated with laminin, expanded for 12 days in EGF/FGF-2, and differentiated in situ as above.

Characterization of NS Cells

Immunocytochemistry was performed using appropriate TRITC or FITC secondary conjugates and nuclear counterstaining with DAPI. Primary antibodies were used at the following dilutions: Nestin (1:10), Vimentin (1:50), Pax6 (1:5), 3CB2 (1:20), RC2 (1:50) (DSHB); TuJ (1:200) (Covance); GFAP (1:300) (poly and mono, Sigma); MAP2 (1:200) (Chemicon and Becton Dickinson); NeuN (1:200), GABA (1:200), Gad65/67 (1:200) (Chemicon); Synaptophysin (1:200) (Sigma); Olig2 (1:5000) (H. Takebayashi); Emx2 (1:2000) (A. Corte); BLBP (1:500) (N. Heintz); prominin/mAb13A4 (1:200) (W. Huttner). Negative controls were ES cells, differentiated NS cells or secondary alone. For RT-PCR, total RNA was extracted using RNeasy kit (Qiagen), and cDNA generated using Superscript II (Invitrogen). PCR was performed for 30 cycles for all markers except β-actin (25 cycles). For metaphase spreads cells were treated with 5 mls of 0.56% KCl for 20 mins, fixed in methanol:acetic acid (3:1) on ice for 15 mins, spread onto glass slides and stained with TOPRO-3 (Molecular probes).

Human Embryo and Foetal Cultures

Research on human tissue with informed consent was approved by the Research Ethics Committee of Lothian Health Board. Frozen supernumerary human embryos were donated for research under licence R0132 issued by the Human Fertilisation and Embryology Authority. Human cortex was dissected from a Carnegie stage 19/20 foetus following elective termination with consent for research under the Polkinghorne guidelines.

Transplants

Foetal surgery was performed as described by Magrassi et al, 1998. Using a glass capillary, $5\times10^4$ cells in a volume of 1 µl of HBSS were injected into the telencephalic vesicles of E14.5 Sprague Dawley rat foetuses exposed under transillumination. Injected foetuses were replaced into the abdominal cavity for development to term. After delivery animals were sacrificed at seven days (Postnatal day (P) 1, n=16) and five weeks (P30, n=8) post transplantation. For adult transplantations, 129 or CD1 mice were placed in a Kopf stereotaxic frame and received an injection of $2\times10^5$ NS cells suspended in 5 µl of HBSS into the striatum (n=22) or hippocampus (n=21). Transplanted mice were sacrificed after two (n=16) and four weeks (n=10) and perfused transcardially with 4% paraformaldehyde. Cryosections (16 µm) were stained with the following antibodies: (mouse): NeuN (1:100) and Ki67 (1:10) (Chemicon), MAP2 (1:200; Becton Dickinson), Nestin (1:5; Ron McKay); (rabbit): βIII tubulin (1:500; Covance); GFAP (1:200; Dako); secondary antibodies, Texas Red (Vector) (Jackson ImmunoResearch) and AlexaFluor 488 (Molecular Probes). Sections were preserved in antifading solution and analysed on Nikon TE2000-S ECLIPSE and Biorad Radiance 2100 confocal microscopes.

Example 2-2

We induced monolayer differentiation of ES cells for 7 days then replated in basal medium (NS-A plus N2) supplemented with EGF and FGF-2. Cells surviving under these minimal conditions (non-permissive for ES cell survival) predominantly associate into floating clusters. After 3-5 days these aggregates were harvested and replated in fresh medium. They attached within 2-3 days and outgrew a morphologically homogeneous population of bipolar cells, named LC1. Upon passaging LC1 cells continued to grow as adherent cultures, often forming lattice networks. They can be continuously and rapidly propagated with a doubling time of approximately 24 hours. LC1 cells display the neural precursor markers nestin and RC2 but expression of the astrocyte differentiation marker GFAP or of neuronal antigens is negligible (FIG. 1A). On exposure to serum or BMP, LC1 cells adopt typical astrocyte morphology within 48 hours and subsequently uniformly express GFAP (FIG. 1A,e). In contrast, cells with neuronal processes appear after replating on laminin without EGF for 5-7 days and then withdrawing FGF-2. These cells express neuronal markers type III β-tubulin, MAP2 (FIG. 1A, f,g) and neuN (not shown). Most neurons stain for GAD67 (FIG. 1A,g) and GABA (not shown) and by 7 days a sub-population show expression of the mature marker synaptophysin (FIG. 1A, h). High numbers of neurons (>35%) are generated even after 115 passages (FIG. 1A,i). Together with the observation that LC1 cells retain a diploid chromosome content at late passages (not shown), this confirms the presence of self-renewing neural stem (NS) cells.

Example 2-3

Figure 1B:
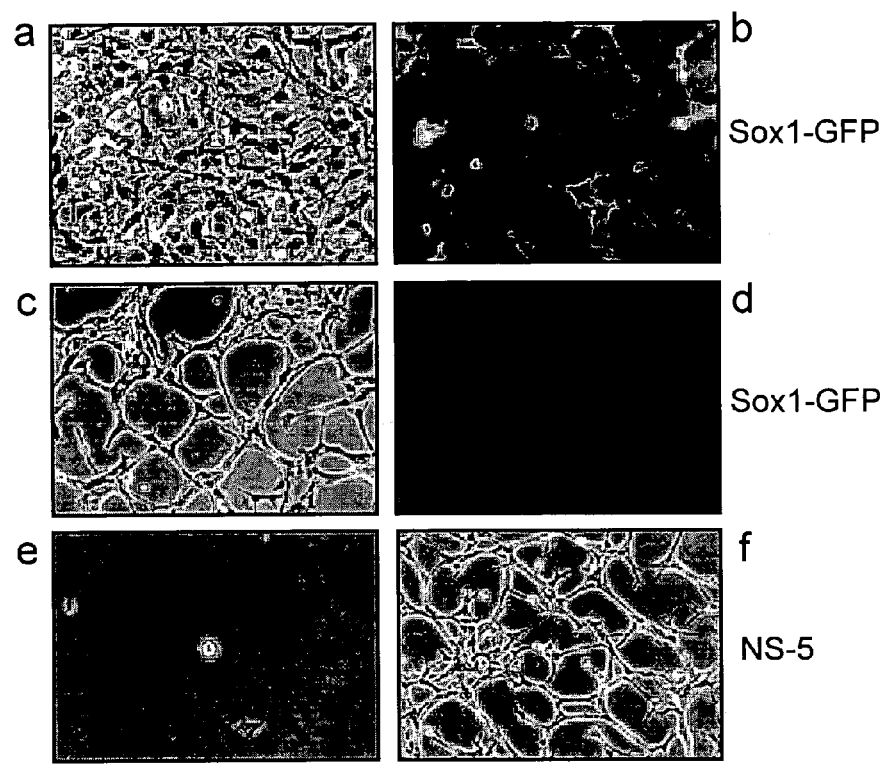
Figure 1C:
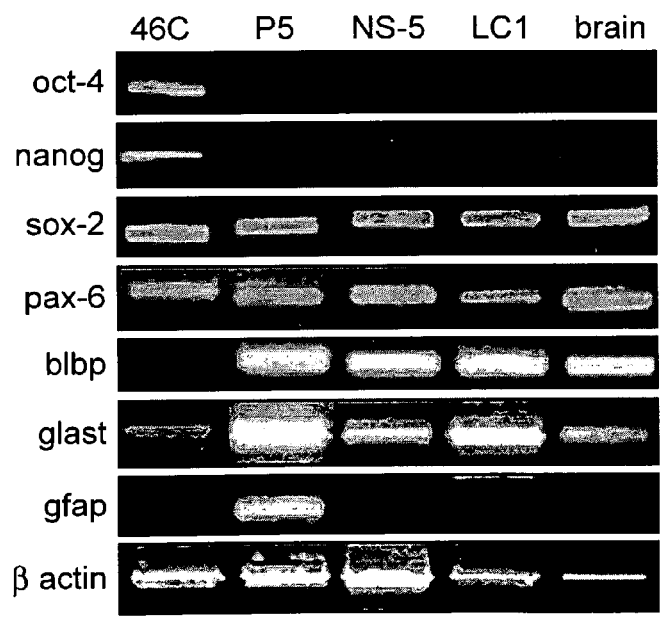

To determine whether cell aggregation is essential for generation of NS cells, we maintained cell attachment throughout the derivation process. For this we exploited lineage selection (Li et al, 1998) using 46C ES cells in which the GFPirespac reporter/selection cassette is integrated into the Sox1 gene, a specific marker of neural specification (Aubert et al, 2003). Transient puromycin selection after differentiation induction yielded a purified population of neural precursors without residual ES cells (Stavridis et al, 2003) (FIG. 1B a,b). FGF-2 and EGF were then applied to the Sox1 expressing neural precursors in enriched medium. Cells remained adherent in this condition. Cellular heterogeneity reduced over 3-4 passages as bipolar cells progressively increased in number and began to form extensive lattices. Intriguingly, expression of Sox1 was lost at this stage (FIG. 1B c,d) but the cells remained positive for Sox2 and nestin. To establish the presence of neural stem (NS) cells, single cells were isolated in Terasaki wells and expanded as adherent cultures (FIG. 1B, e,f). Initially 5 clonal lines were derived of similar morphology and growth characteristics to the bulk LC1 population. These cells lacked detectable expression of the pluripotency factors Oct4 and Nanog, and also of the early neural marker Sox1, but retained the pan-neuroepithelial markers Sox2 and nestin (FIG. 1C). NS cells were thus generated through a Sox1 positive early neuroectodermal precursor via continuous adherent culture.

Example 2-4

Figure 1D:
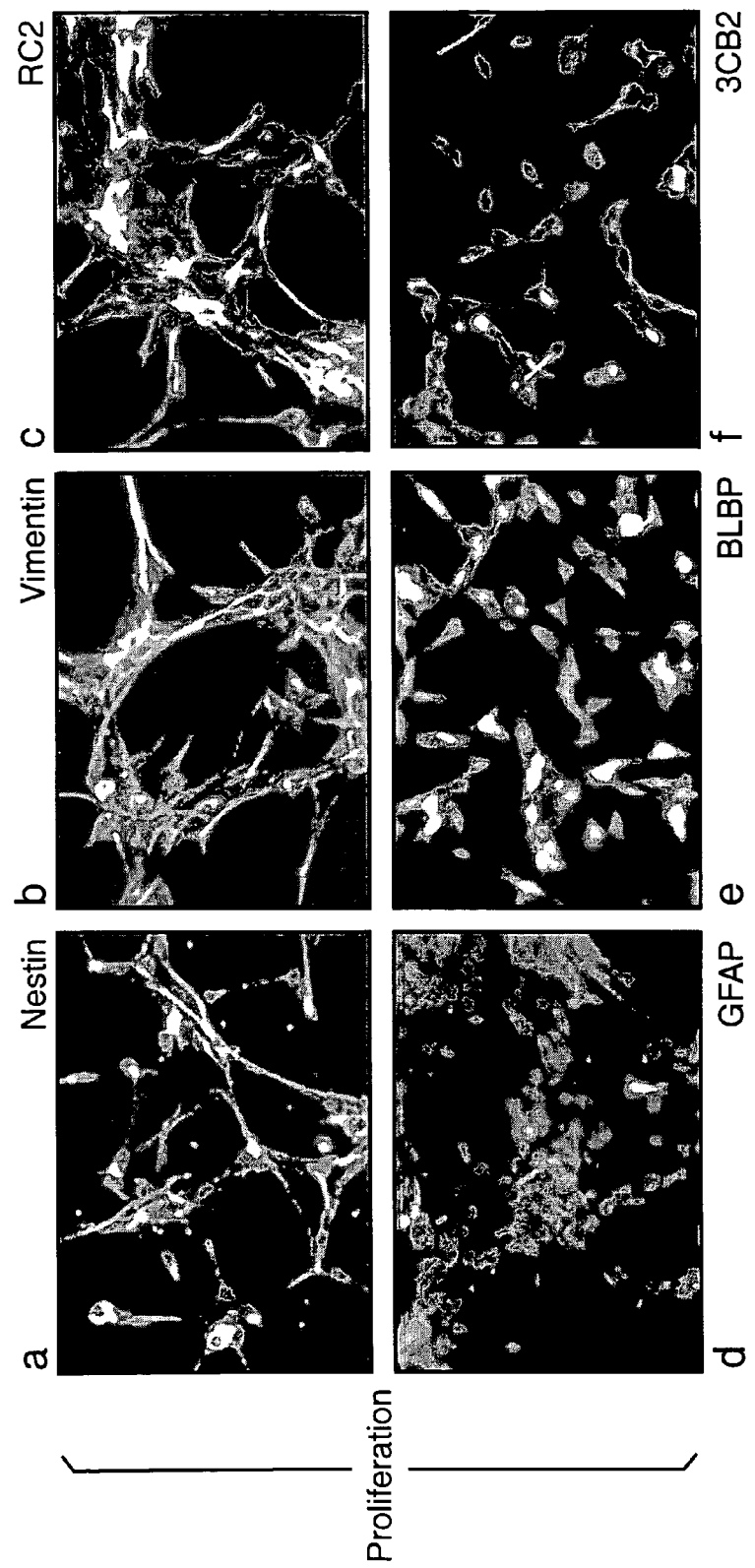
Figure 1F:
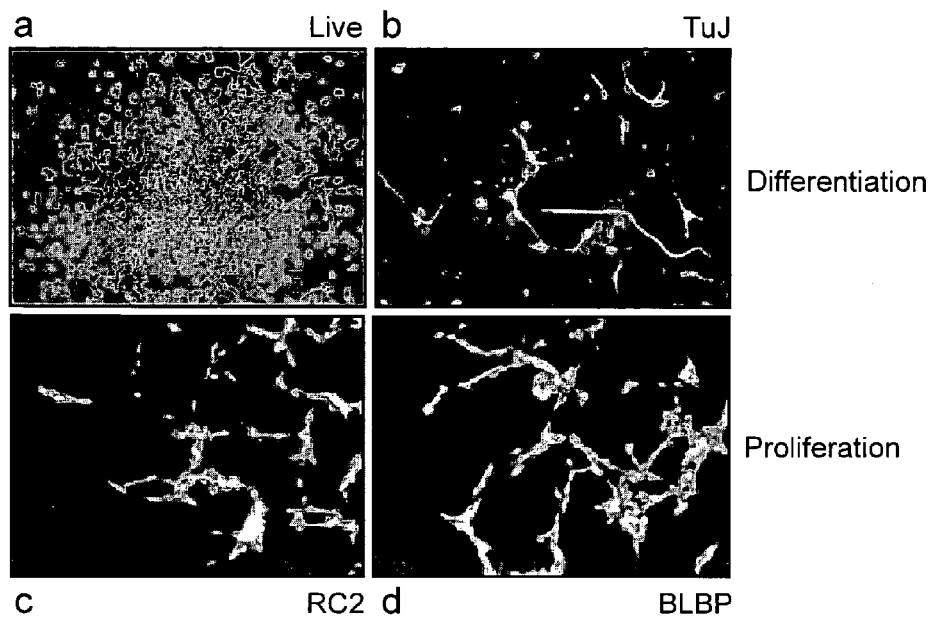
Figure 1G:
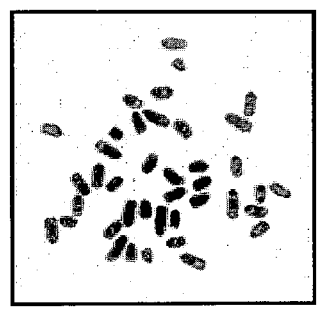

Clone NS-5 was examined in further detail and found to express Pax6, Glast, and BLBP mRNAs, and to be immunopositive for RC2, vimentin, 3CB2, SSEA1/Lex1 and prominin (FIG. 1D). This set of markers is considered diagnostic for neurogenic radial glia, the precursors of both neurons and astrocytes during development of the nervous system (Campbell et al, 2002; Hartfuss et al, 2001). As with uncloned LC1 cells, NS-5 cells were competent for astrocyte and neuronal differentiation (FIG. 1E). NS-5 cells plated at clonal density in EGF plus FGF-2 gave rise to colonies of bipolar cells. Every colony showed expression of RC2 and BLBP in virtually all cells and absence of GFAP (FIG. 1F, c,d). These subclones could be picked and continuously expanded. To determine the frequency of cells within NS cultures that are capable of neuronal differentiation we again plated NS-5 cells at clonal density, expanded for 12 days in EGF/FGF-2 followed by FGF-2 alone for 5 days, then a further 7 days without growth factor. Every colony (126/126) produced TuJ positive cells (FIG. 1F, b). These data indicated that all colony forming cells in NS cultures were competent for neuronal differentiation. Finally, like LC1, NS-5 cells maintained a diploid chromosome complement (FIG. 1G) and represented a non-transformed clonal neural stem (NS) cell line that self-renewed without a requirement for a complex cellular microenvironment.

Example 2-5

To assess whether the serum-free monolayer induction protocol is a prerequisite for NS cell generation, ES cells were induced to differentiate by embryoid body formation and exposure to retinoic acid in serum-containing medium (Bain et al, 1995). Aggregates were subjected to Sox2 lineage selection (Li et al, 1998; Billon et al, 2002) with G418 for 48 hours then replated in the presence of FGF-2 and EGF without serum. Following attachment, Sox2 positive, nestin positive, cells proliferated that displayed the bipolar morphology and lattice growth typical of NS cells plus capacity for astrocyte and neuronal differentiation after multiple passages (data not shown). Thus NS cells were derived from embryoid bodies.

Example 2-6

Figure 2A:
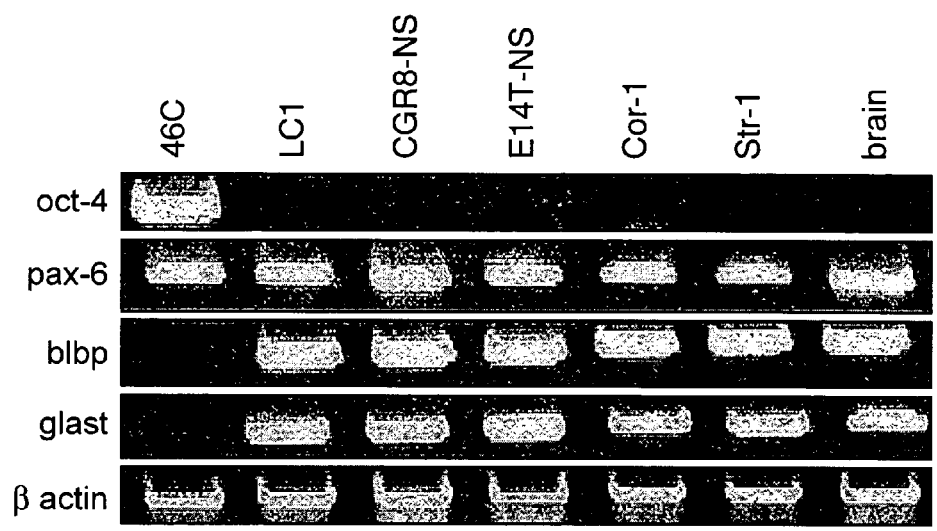
FIG. 2 shows NS cells can be derived from various ES cell line and foetal forebrain.
Figure 2B:
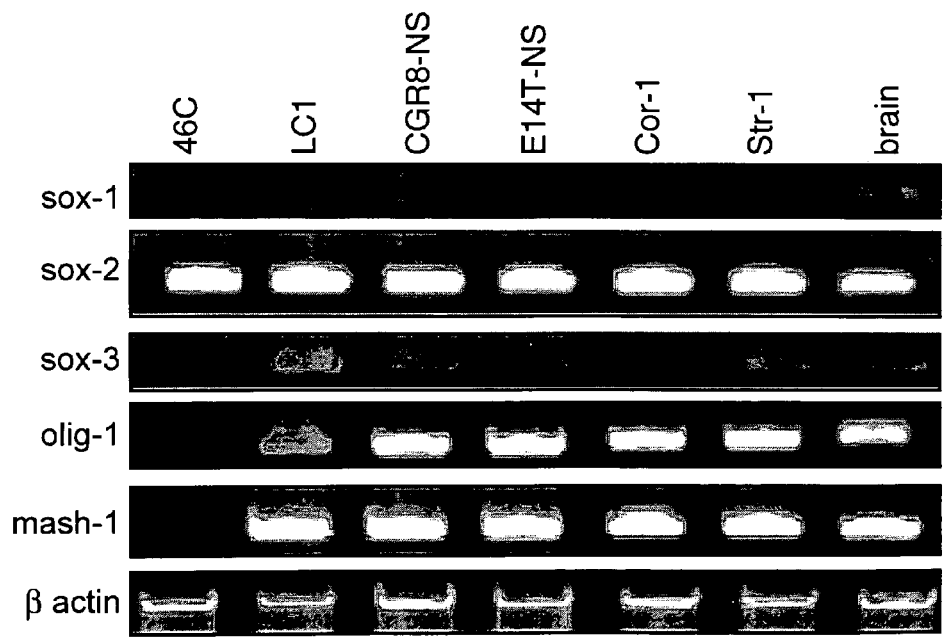

NS cells were derived using monolayer induction without lineage selection as described for LC1 from three independent ES cell isolates, E14TG2a, CGR8 and R1. All NS lines examined expressed nestin and RC2 in at least 95% of cells. More detailed inspection of CGR8 and E14TG2a derived NS cells showed the full panel of radial glia markers (FIG. 2A), the neural precursor markers Sox2 and Sox3, plus the bHLH transcription factors Olig2 and Mash1 (FIG. 2B). Down-regulation of Sox1 but maintenance of Sox2 was a striking feature of these NS cells, in view of the postulated determinative function of these transcription factors (Pevny et al, 1998). Thus whilst Sox1 marks all neuroectodermal precursors, it was not retained in stem cells where Sox2 is likely to play a key role. The NS cells also expressed Emx2 which is implicated in expansion of neural precursor cells (Hein et al, 2001; Galli et al, 2002). All NS cultures tested underwent astrocyte and neuronal differentiation assessed by both morphology and immunostaining (FIG. 2C).

Example 2-7

In light of their apparent relationship to radial glia, we examined whether NS cells resulted from the pre-adaptation of ES cells to ex vivo propagation or could be derived from foetal neural tissue. Primary foetal CNS cells from E16.5 foetal brain adhered poorly to plastic in basal medium plus growth factors and spontaneously formed aggregates. After 6-7 days these aggregates settled onto gelatin-coated plastic. Fourteen days later, outgrowths were trypsinised and plated onto gelatin-coated plastic. In three separate experiments cells morphologically identifiable as NS cells proliferated and were subsequently expanded into continuous cell lines. These foetal brain derivatives expressed the same radial glia and neurogenic markers as the ES cell derived NS cells (FIG. 2A,B) and showed consistent mRNA profiles. They were likewise competent for astrocyte and neuronal differentiation (FIG. 2C). Cortex-derived Cor-1 cells were plated as single cells then colonies subjected to sequential growth factor withdrawal as described for NS-5. Every colony produced TuJ positive neurons. This indicated that all clonogenic cells in the Corn culture were neurogenic. Cor-1 cells were also readily sub-cloned and continuously expanded from individual cells, indicative of self-renewal. Thus NS cells were derived from foetal brain and shared the key properties of ES cell derived NS cells.

Most NS cells had the elongated bipolar morphology, lamellate extensions, end-feet and oval nuclei anticipated for radial glia (Rakic, 2003). Flattened and compact cells with short extensions were also present. Immunostaining for the metaphase marker phosphorylated histone H3 indicated that the compact cells are mitotic. Time lapse videomicroscopy confirmed the dynamic change in morphology prior to cell division. In addition, the time lapse revealed that NS cell undergo interkinetic nuclear migration, a well-characterized feature of neuroepithelial and radial glia cells in vivo.

The NS cells were hence continuously expandable in vitro analogues of neurogenic radial glia.

Example 2-8

Frozen/thawed passage 40 mouse neurospheres were allowed to attach to gelatin-coated plastic in NS expansion medium. Bipolar cells outgrew that are indistinguishable from NS cells. These cells can be serially propagated as uniformly RC2 positive, GFAP negative, populations and then induced to differentiate into astrocytes or neurons.

Example 2-9

We investigated the behavior of NS cells upon transplantation into mouse brain. ES cell derived LC1 cells transduced with a lentiviral eGFP expression vector were introduced into the developing brain by intra-uterine injection at E14.5 (Magrassi et al, 1998). Animals were sacrificed after birth and the presence of eGFP positive cells examined in brain sections. NS cell progeny had migrated into various brain regions. Immunohistochemical analyses revealed co-expression of eGFP with the precursor marker nestin, neuronal markers TuJ, NeuN and MAP2, and in lesser numbers with GFAP. NS cells were also injected into the adult mouse striatum. In this case GFP-positive cells remained localised to the vicinity of the injection site. Four weeks after grafting, 44.4±5.7% of GFP expressing cells had neuronal morphology and were immunopositive for MAP2, 37.4±6.1% expressed GFAP, and 4.2±1.9% retained expression of nestin (FIG. 3). The proliferative marker Ki67 was detected in only 1.0±0.6% of GFP positive cells indicating that NS cells withdraw from the cell cycle in vivo. Consistent with this we observed no histological evidence of un-regulated proliferation or tumour formation in a total of 35 brains examined one month after transplantation. Furthermore, NS cells grafted to mouse kidney capsules did not proliferate or give rise to teratomas. These data indicated that NS cells can survive and differentiate in both foetal and adult brain environments and unlike ES cells (Brustle et al, 1997), they do not give rise to teratomas. Moreover, the relatively high frequency of neuronal differentiation is in marked contrast to grafts of passaged neurospheres (Rossi et al, 2002).

Example 2-10

Figure 4B:
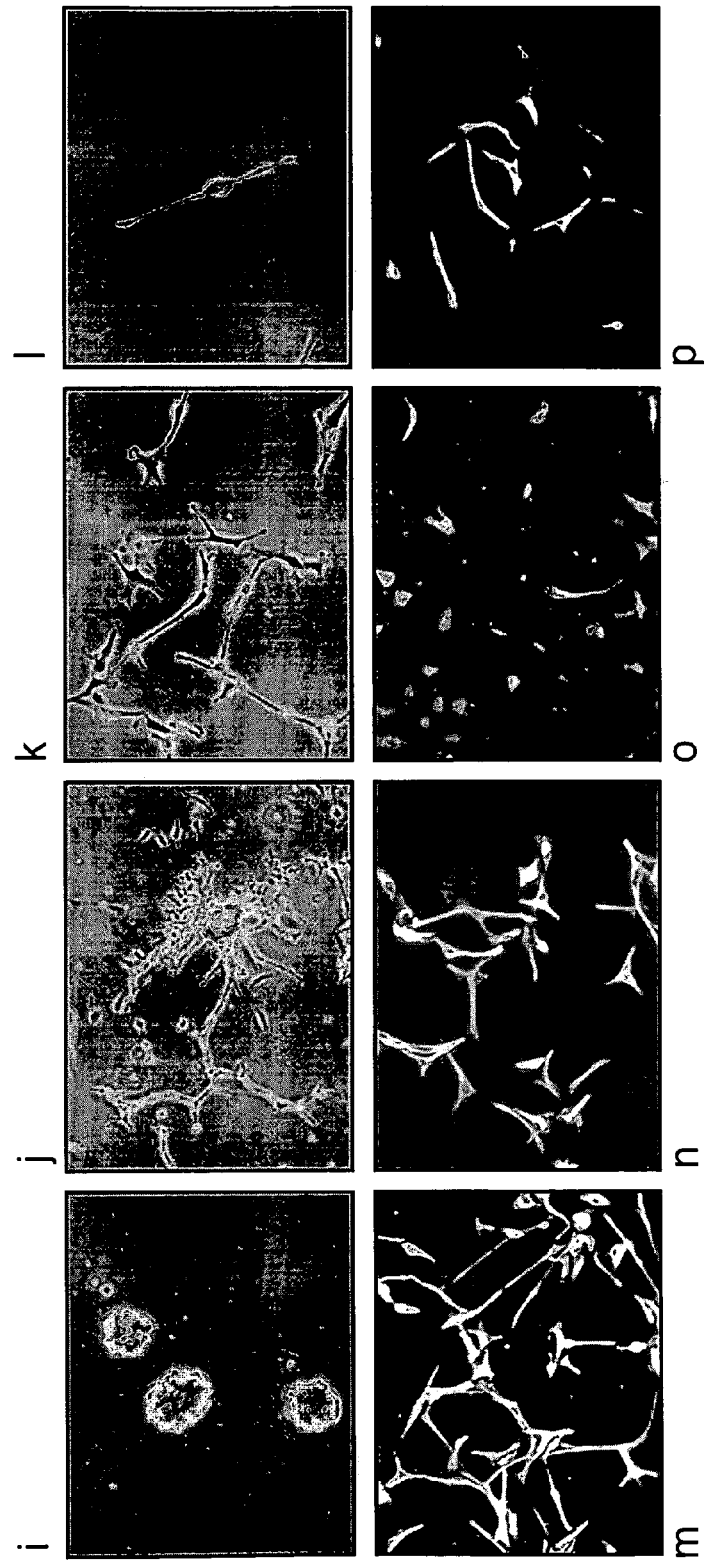
Figure 4C:
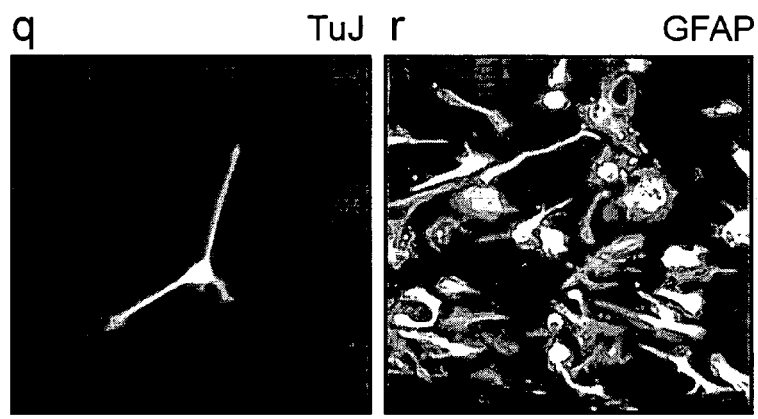

Finally we investigated whether similar NS cells could be isolated from human sources. In the process of deriving human ES cells from donated supernumerary embryos, we observed after 5-6 weeks of culture extensive differentiation into rosette structures typical of neuroepithelial cells. These cells were transferred into NS expansion medium. After a further 3-4 weeks bipolar cells similar to NS cells emerged from these cultures (FIG. 4A) and have been continuously cultured for 5 months. We also sourced Carnegie stage 19-20 human foetal cortex tissue from an elective termination. Dissociated cells initially formed floating aggregates that after 7 days were replated and allowed to attach to gelatin-coated plastic as for derivation of NS cells from mouse foetal brain. A proliferating culture was established (FIG. 4B). Human NS cultures from both ES cells and fetal tissue were characterized by the presence of flattened cells associated with the bipolar cells. However, all cells expressed immature precursor markers nestin, vimentin and 3CB2 (FIG. 4B). Time lapse monitoring confirmed that the two cell morphologies are plastic and interconvertible. These human cells also exhibited low levels of GFAP consistent with the activity of the human GFAP promoter in radial glia (Rakic, 2003; Malatesta et al, 2000). They proliferated more slowly than the mouse cells, with doubling times of several days. After sequential withdrawal of EGF and FGF-2 they appeared to generate immature neuronal cells (FIG. 4C). Cells of typical astrocyte morphology with intense GFAP immunoreactivity were produced after passaging in serum (FIG. 4C).

Example 3

The electrophysiological properties of NS cells in culture were investigated during in vitro differentiation by employing the whole-cell variant of the patch-clamp technique, in order to know whether, following specific treatments, these cells could be efficiently transformed into mature and functional neurons from an electrophysiological point of view.

Solutions for Electrophysiological Recording

Seals between electrodes and cells were established in a bath solution consisting of (in mmoles/l): 155 NaCl, 1.0 $CaCl_2$, 1 $MgCl_2$, 3.0 KCl, 10 glucose, 10 HEPES/NaOH (pH 7.4). After establishing the whole-cell configuration, for current-clamp recording and for total current recording in voltage-clamp, the pipette filling solution contained (in mmoles/l): 128 KCl, 10 NaCl, 11 EGTA, 4 Mg-ATP, 10 HEPES/KOH (pH 7.4). For the study of voltage-gated $Na^+$ channels under voltage clamp conditions, the patch pipette was filled with (in mmoles/l): 130 CsCl, 10 NaCl, 20 TEA-Cl, 10 EGTA, 2 $MgCl_2$, 4 Mg-ATP, 10 HEPES/CsOH (pH 7.4) and the extracellular solution contained (in mmoles/l): 130 NaCl, 2 $CaCl_2$, 2 $MgCl_2$, 10 glucose, 5 tetrethylammonium-Cl, $CdCl_2$ 0.2, 10 HEPES/NaOH (pH 7.4). For the study of voltage-gated $Ca^{2+}$ channels, the patch pipette was filled with (in mmoles/l): 120 CsCl, 20 TEA-Cl, 10 EGTA, 2 $MgCl_2$, 4 Mg-ATP, 10 HEPES/CsOH (pH 7.4) and the extracellular solution contained (in mmoles/l): 130 NaCl, 10 $BaCl_2$, 10 glucose, 5 tetrethylammonium-Cl, 10 4-AP 1, TTX $10^{-3}$, HEPES/NaOH (pH 7.4).

Patch Clamp Recording

Ionic currents were recorded under voltage-clamp conditions using the patch-clamp whole-cell configuration (19) at room temperature (20-24° C.) with an Axopatch 200B patch-clamp amplifier (Axon Instruments Inc., Burlingame, Calif.) and digitized at sampling intervals of 26-100 μsec using a Digidata 1322A A/D converter (Axon Instruments Inc., Burlingame, Calif.) interfaced with an IBM-compatible PC. Stimulation, acquisition, and data analysis were carried out using the following software pachages: pClamp 9 (Axoninstruments Inc., Burlingame, Calif.) and ORIGIN 6 (Microcal Software Inc., Northampton, Mass.). For voltage-clamp experiments linear components of leak and capacitive currents were first reduced by analogue circuitry and then almost completely canceled with the P/N method. Patch pipettes were made from borosilicate glass tubing and fire polished. Pipettes had a final resistance of 3-4 MΩ when filled with internal solution. Currents were filtered at 5 KHz.

Figure 5A:
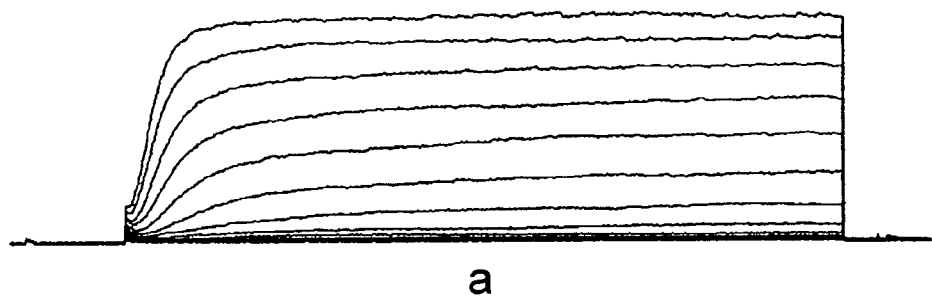
FIG. 5 shows electrical activity under voltage- and current-clamp conditions of NS cells cultured in differentiating medium.
Figure 5A:
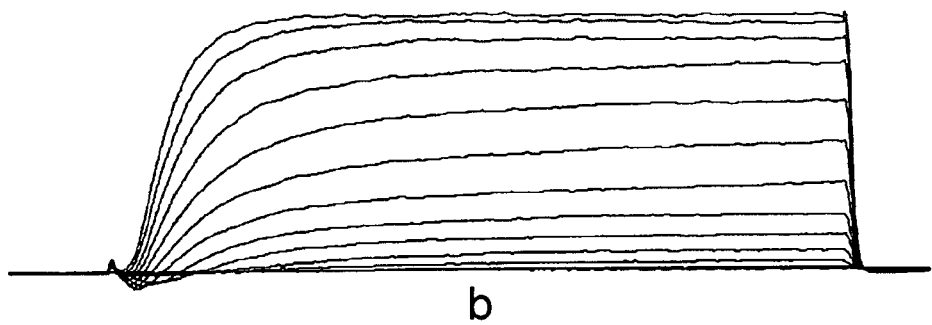
Figure 5A:
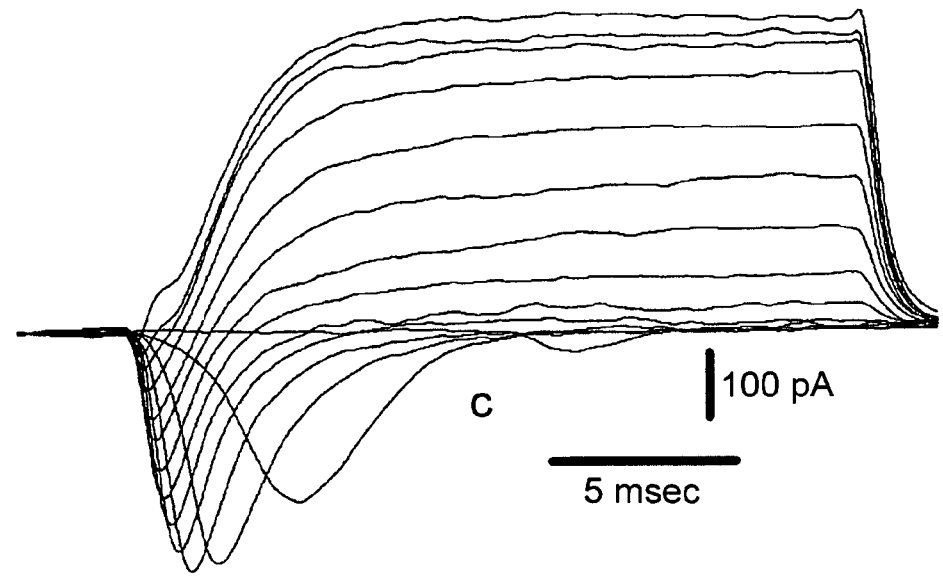
Figure 5B:
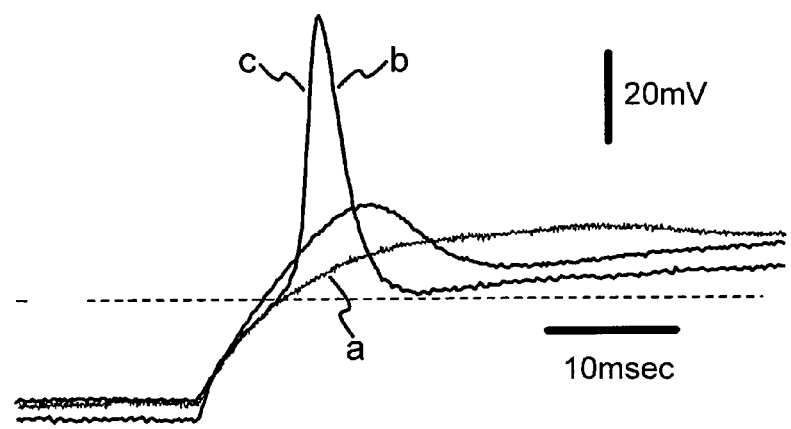
Figure 5C:
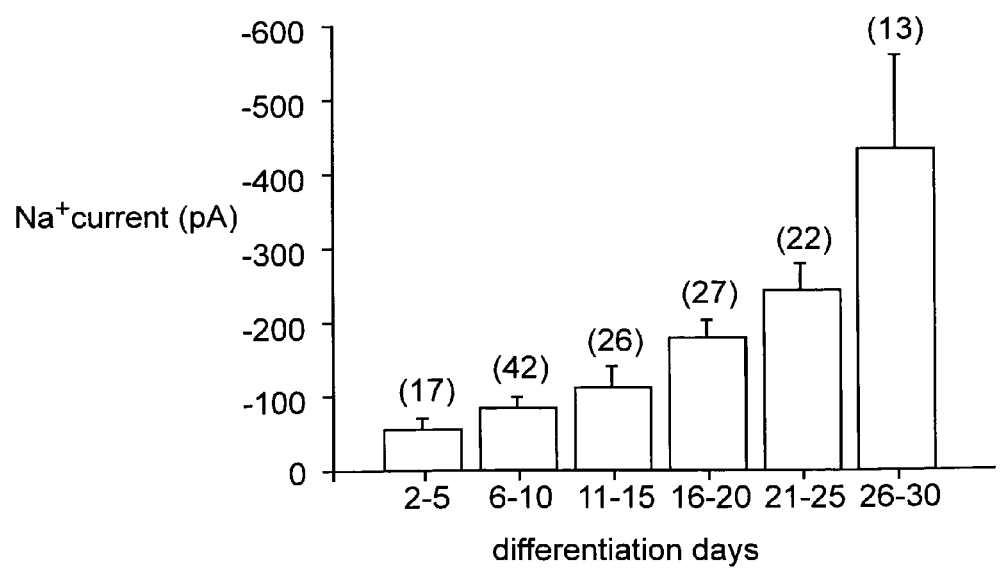
Figure 5D:
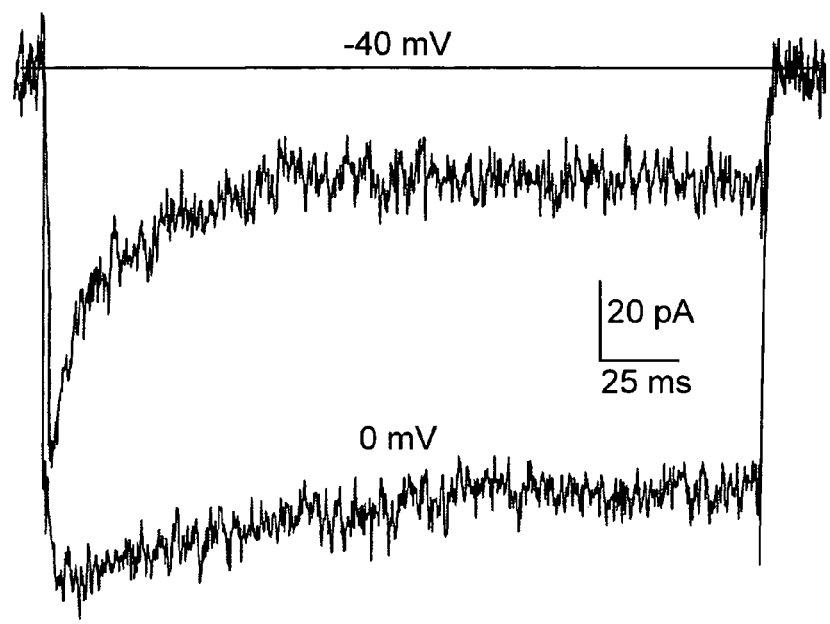
Figure 5E:
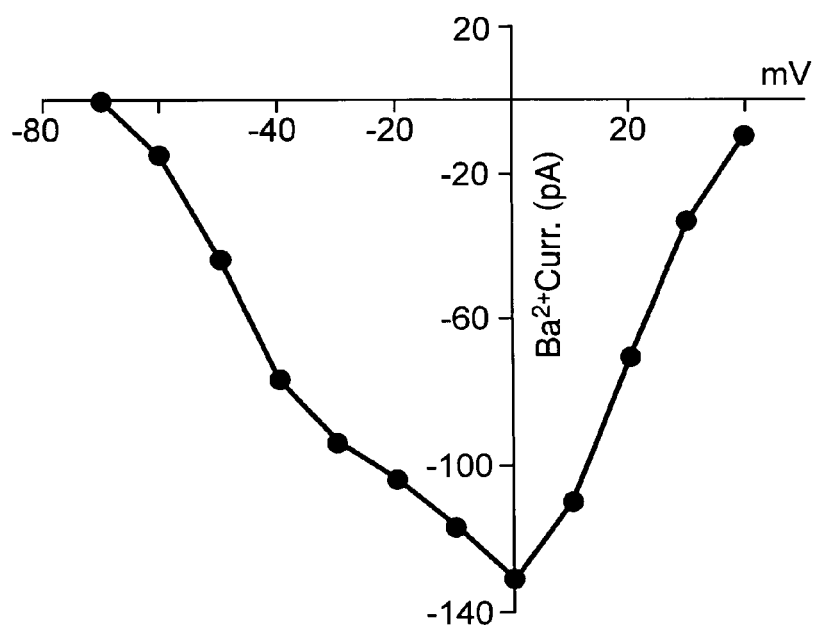

FIG. 5A shows current recordings obtained during whole-cell voltage-clamp steps to depolarising test potentials in three NS cells at different stages of in vitro differentiation (cultured respectively for 6, 20 and 30 days in a differentiating medium), using bath and pipette filling solutions suitable for the isolation of both inward ($Na^+$) and outward ($K^+$) voltage-gated ionic currents. From a simple inspection of the current tracings it is evident that a sizeable outward voltage-gated current is already present at early stages of in vitro differentiation (6 days, trace a). This current, blocked by application of an extracellular saline containing 5 mM tetraethylammonium-Cl, has the features of a delayed-rectifier $K^+$ current. Its amplitude increased only slightly at later stages of differentiation (20-30 days, traces b and c respectively). By contrast, the amplitude of the inward current, negligible after six days, increases dramatically by increasing the time of exposure to the differentiating medium. FIG. 5B shows the voltage responses elicited following intracellular injection of rectangular depolarizing current stimuli between 70 and 300 pA from a holding potential of about −80 mV, after switching from voltage-clamp to current-clamp mode in the same cells shown in FIG. 5A. Indeed, the increase in amplitude of the voltage-gated inward current reflects the capacity of the differentiating cells to elicit action potentials. In fact, the cell exposed for only six days to the differentiating agents and showing a negligible inward current was not able to elicit a regenerative voltage response (trace labelled with (a) in FIG. 5B). By contrast, an overshooting action potential with a relatively fast depolarisation rate could be elicited in the cell cultured in differentiating medium for thirty days (trace labelled with (c) in FIG. 5B) and displaying a large inward current (trace c in FIG. A). An intermediate situation, with an abortive action potential, was found in the cell treated for twenty days with the differentiating agents (trace labelled with (b) in FIG. 5B) and displaying a moderate inward current (trace b in FIG. A). From this preliminary analysis it turns out that the excitability properties of these cells are strictly correlated to the magnitude of the inward voltage-gated conductance. For a quantitative analysis of this conductance as a function of the time of exposure to the differentiating medium, the inward currents were elicited using cells at different stages of differentiation and applying intra- and extracellular salines specific for the study of the activity of voltage-gated $Na^+$ channels (see methods). At any time of cell differentiation the fast inactivating inward current was completely blocked by the selective Na channel blocker tetrodotoxin (1 $\mu M$) and peaked at a test potential between −20 and −10 mV, showing the typical features of voltage-gated $Na^+$ currents in neurons (data not shown). In FIG. 5C the development of the $Na^+$ current amplitude at −20 mV as a function of the time of exposure to the differentiating medium is shown. Interestingly, the increase of the $Na^+$ conductance well correlates with the increasing cell exposure to the differentiating medium. Indeed, on average the $Na^+$ current amplitude increases of about a factor ten within 30 days of treatment (from −55±14 pA (n=17) during the first 5 days to −434±135 pA (n=13) for more than 25 days). In the same way, the regenerative potential (the $\Delta V$ measured between the threshold and the peak) elicited by the $Na^+$ current under current clamp conditions ranged between 0 and +20 mV during the first 15 days of in vitro differentiation (n=6), whereas following more than 25 days of treatment it reached values between +30 and +70 mV (n=6). On the whole, the excitability properties and those of the underlying voltage-gated $Na^+$ conductance found in NS cells treated longer than 25 days with the differentiating medium are typical of neurons developing toward their adult phenotype. Another feature corroborating the previous conclusions is the presence of voltage-gated $Ca^{2+}$ channel conductances in most of the tested cells following exposure to the differentiating medium for at least seven days or longer. FIG. 5D shows sample tracings obtained by membrane depolarization to the indicated test potentials from the same cell bathed in 10 mM $Ba^{2+}$. The fast activating and relatively fast inactivating ($\Box_h$=21 ms) current component elicited at −40 mV is reminiscent of the neuronal LVA $Ca^{2+}$ channel current (Carbone and Lux, 1987). By contrast, the $Ba^{2+}$ current elicited at 0 mV, displaying a slow ($\Box_h$=73 ms) and incomplete inactivation, has the typical features of the neuronal HVA $Ca^{2+}$ channel current. The presence in this cell of two distinct, LVA and HVA, $Ca^{2+}$ channel conductances is confirmed by the current-voltage relationship of FIG. 5E. On average the LVA current peaked at −40 mV, while the I/V relationship for the HVA current peaked at 0 mV. A HVA $Ba^{2+}$ current was detectable in 19 out of 27 cells, while a LVA current component was measured in 60% of the cells already expressing a HVA $Ca^{2+}$ current (n=13).

This data shows that neurons produced from neural stem cells of the invention can function: they can fire action potentials, the hallmark of active neurons.

Thus, according to the invention, we have derived and homogenously propagated defined NS cells as differentiated progeny of ES cells and foetal brain extracts. The NS cells proliferated clonally in simple adherent monoculture and remained diploid. After prolonged expansion, they differentiated efficiently into neurons and astrocytes both in vitro and on transplantation into the adult brain. NS cells also formed oligodendrocytes in vitro. NS cells uniformly expressed morphological and molecular features of radial glia, foetal precursors of neurons and astrocytes. We were able to establish adherent NS cell lines from mouse and human foetal brain.

Example 6

NS cells were obtained from mouse ES cell and foetal cortex using the protocol below. The derived NS cells uniformly expressed radial glia markers. NS cells derived specifically from CGR8 ES cells or from E16 foetal cortex (internal reference: Cor-1 and clonal derivative Cor-1.3) were analysed for expression of the indicated markers by immunochemistry. Examination at high power showed that the radial glia markers were each expressed in almost all cells whilst they were uniformly negative for GFAP.

Example 7

NS cells were derived from expanded mouse foetal forebrain neurospheres using the protocol below. An NS line derived from a long-term foetal neurosphere culture (40 passages) exhibited identical morphology to ES-derived NS lines, expressed neural precursor cell/radial glial marker immunoreactivity, and could differentiate into neurons and astrocytes. This showed that the NS cells obtained from fresh foetal neurospheres were the same as those from neurospheres frozen down and then grown as neurospheres for a long time.

Example 8

LC1 mouse NS cells were transplanted into foetal rat brain. Confocal images of NS cells, lenti-virally transduced with eGFP, were taken one week after transplantation into the ventricle of E14.5 rats. Donor cells migrated from the ventricle into the parenchyma in clusters and as single cells. Grafted cells showed co-localization of eGFP and the neuronal marker MAP2, the astroglia marker GFAP or the progenitor cell marker nestin. Thus, the NS cells migrated and differentiated after transplantation in the foetal rat brain.

Example 9

Protocols For Derivation and Manipulation of NS Cell Lines

We devised the following protocols for derivation and manipulation of NS cell lines.

Derivation of Mouse NS Cell Lines from ES Cells

ES cells can efficiently be converted to Sox1 expressing neural progenitors in adherent monolayer culture [P1]. Detailed protocols and troubleshooting and for this ES cell differentiation are described elsewhere [P2]. Briefly, ES cells are routinely cultured under feeder-free conditions in medium supplemented with 10% foetal calf serum and 100 U/ml recombinant leukaemia inhibitory factor (LIF) on gelatin-coated tissue culture plastic [P3]. Undifferentiated ES cells are expanded to ~80% confluence in a T75 flask (Iwaki), trypsinised and resuspended in N2B27 media [P2]. Cells are plated onto 9 cm plates (Iwaki) that have been coated with a 0.1% gelatin solution (Sigma) for at least 10 mins then allowed to dry. As initial plating density is a crucial parameter for efficient neural induction, and can vary between ES cell lines, we routinely seed several different cell densities (0.8×$10^6$, 1×$10^6$ and 1.2×$10^6$) per plate. Culture medium is changed each day, in the process removing detached or dead cells. Under these conditions 50-80% of cells will undergo neural lineage specification within 4-5 days, and with overt neuronal differentiation detectable from day 5 onwards.

Conversion of heterogeneous progenitor cultures to homogeneous NS cell lines can be achieved as follows. Day 7 differentiated cultures are trypsinised and 2-3×$10^6$ cells are re-plated into an uncoated T75 flask in NS expansion media, comprising NS-A media (Euroclone) supplemented with L-glutamine, 2 mM final (Gibco), modified N2 supplement (freshly prepared in house) [P2] and 10 ng/ml of both mouse EGF (Peprotech) and human FGF-2 (Peprotech). Expansion media can be stored at 4° C. for up to 4 weeks. Within 2-3 days the flask will contain many thousands of floating aggregates in suspension culture (absolute number varies according to efficiency of initial ES cell differentiation). Cell aggregates are harvested by mild centrifugation or allowed to settle under gravity in a 30 ml universal tube for 10 mins. This step removes debris and dead cells, thus enriching for NS cell founders, and ensures complete media exchange. Cells are replated in 10 ml of fresh NS expansion medium onto a gelatin coated T75 flask (Iwaki). After a further 3-7 days, cell aggregates will attach to the flask and shortly thereafter cells outgrow with characteristic bipolar NS cell morphology. Following extensive outgrowth of cells (a further 3-4 days) the entire population is trypsinised and re-plated as single cells onto a gelatin coated T75 flask in expansion medium. Cells grow very rapidly (doubling time ~25 hrs) and remain adherent. Within several passages residual differentiated and blast cells are eliminated (monitored by GFAP and TuJ1 immunostaining) and cultures are uniformly positive for NS cell markers.

For 46C ES cells (Sox1-GFP-IRES-pac knock-in) [P4] a transient selection with puromycin (0.5 μg/ml) can be used to eliminate non-neural cells and derive NS cells via continuous adherent culture. 46C ES cells (1×$10^6$) are plated in N2B27 media onto a gelatin coated 9 cm dish to induce neural commitment. Six days later puromycin is added for 48 hrs. The enriched Sox1 expressing cell population (~3-5×$10^6$) is then re-plated in N2B27 medium containing EGF (10 ng/ml) and FGF-2 (10 ng/ml) on gelatin coated 9 cm plates. The initially morphologically heterogenous Sox1 expressing population progressively acquires a Sox1 negative character and after 3-4 passages uniform NS cell morphology and marker expression.

Derivation of Mouse NS Cell Lines from Foetal CNS and Neurospheres

Cell clusters form in suspension upon dissociation of foetal E16.5 cortex and primary culture in NS cell expansion media. These primary aggregates can be readily converted into adherent NS cell lines by plating onto gelatin-coated substrate in expansion medium. In order to promote attachment, it is important that debris/dead cells are first effectively removed by sedimentation and medium is exchanged completely. Cell aggregates will attach and outgrow over 2-5 days. Outgrowing cells can subsequently be trypsinised to single cells, re-plated and propagated in NS cell expansion medium. From passaged foetal neurospheres [P5], NS cells can conveniently be established by dissociation and plating directly on gelatin coated plastic in NS expansion medium. During the initial few passages the derived NS lines have a tendency to aggregate, detach from the flask and re-form neurospheres, particularly if the cell density becomes high. Cultures should therefore be passaged at or below 50% confluence. The tendency to spontaneously aggregate is variable, but is generally reduced upon further passaging, or through establishment of clonal cell lines.

Passage and Expansion of NS Cells

Once established, NS cells are propagated in NS expansion media. NS cells are grown on gelatin coated plates/flasks and are routinely split 1 in 2 to 1 in 5. NS cells have a doubling time of around 25 hrs. Cells are passaged using trypsin/EDTA or through incubation with calcium magnesium-free PBS (Sigma). For establishment of clonal lines, single cells can be deposited in gelatin-coated microwells in expansion medium. Less rigorously, cells can be plated at very low density, 1000 cells per 9 cm dish. Colonies appear within two weeks and can be picked and expanded.

Cryopreservation and Recovery of NS Cells

NS cells are readily recovered following freezing/thawing. Routinely we trypsinise a 60-90% confluent T75 flask, and resuspend the pellet into 1.5 ml NS expansion media plus 10% DMSO. This is then split into 3×1 ml cryotubes (Nunc) and stored at −80° C. NS cells are recoverable following more than 6 months storage in these conditions. For long term storage frozen vials are transferred to liquid nitrogen. NS cells are thawed by rapidly bringing the vial to 37° C. followed by transfer to 10 ml of pre-warmed NS expansion media. Cells are pelleted and then resuspended in fresh expansion media to remove DMSO. Cell recovery following cryopreservation is >95% for NS cells.

Astrocyte and Neuronal Differentiation of NS Cells

Rapid differentiation of NS cells to GFAP positive astrocytes occurs within 2 days of exposure of NS cells to BMP4 (10 ng/ml) or 1% FCS in NS-A (with N2, without EGF/FGF) on gelatin coated flasks/plates. Cell density is not a crucial parameter for astrocyte differentiation.

For neuronal differentiation NS cells are harvested using Accutase (Sigma) or calcium/magnesium-free PBS to detach cells and 0.5-1.0×$10^4$ cells are re-plated into each well of a poly-ornithine/laminin coated 4-well multidish plate (Nunc) in NS-A medium supplemented with FGF-2 (5 ng/ml), modified N2, and B27 (Gibco). We find that the NS-A basal medium is more permissive for neuronal differentiation, than other basal media. A half volume of medium is replaced every 2-3 days to maintain conditioning of medium. After 7 days in these conditions we exchange media to NS-A mixed with Neurobasal medium (Gibco) in a ratio of 1:1 supplemented with 0.25×N2 plus B27 and without EGF or FGF. This formulation promotes further neuronal differentiation and maturation. For longer term cultures of neurons (beyond 14 days) we exchange media to Neurobasal supplemented with B27 without N2 in the presence of BDNF (10 ng/ml).

Culture and Neuronal Differentiation of Human NS Cells

Human NS cells are expanded on 0.1% gelatine (Sigma) coated flasks/plates in expansion media as for mouse NS cells additionally supplemented with 100 U/ml recombinant human leukaemia inhibitory factor (LIF). Cells have a doubling time of approximately 1 week. They are passaged with trypsin once reaching ~30% confluence and split 1 in 2. Overgrowth should be avoided to maintain monolayer culture and prevent aggregation and detachment.

For neuronal differentiation, human NS cells are harvested using Accutase (Sigma) and around $1 \times 10^4$ cells re-plated into each well of poly-ornithine/laminin (Sigma) coated 12-well plate (Iwaki) in expansion media. Cells are expanded until they reach around 80% confluent. Neuronal differentiation is induced by removing EGF and LIF from expansion media. After 7 days in the absence of EGF and LIF, exchange media to NS-A mixed with Neurobasal media in a ratio of 1:1 (Gibco) supplemented with 0.5×N2, B27, FGF2 (5 ng/ml), and BDNF (10 ng/ml). After a further 7 days in these conditions, media is switched to Neurobasal media supplemented with B27 and BDNF (10 ng/ml) without N2 or FGF-2. Half the medium is exchanged every 2 or 3 days as for mouse NS cells throughout this protocol. After a further 10 days cells of neuronal morphology immunoreactive with TuJ1 and MAP2 represent up to 40% of total cell numbers. Significant numbers of astrocytes are also generated, in contrast to the mouse NS cell protocol for neuronal differentiation in which few GFAP positive cells emerge.

The invention thus provides methods and media for obtaining and maintaining neural stem cells of many species in a symmetrically-dividing, undifferentiated state. The invention has been carried out using cells obtained or extracted from ES cell, foetal and adult sources. In all cases the resultant cells obtained by following the methods described herein look and behave substantially the same; they all can be maintained in high purity cultures over high numbers of, e.g. hundreds of, doublings with a high proportion of the cells retaining the ability to form neurons and glia. Specifically, NS cells have been successfully obtained from human (ES, foetal CNS), mouse (ES, foetal CNS, adult CNS) and rat (foetal CNS). Mouse neural stem cells have been grown in culture in pure populations and after being transplanted grew without forming tumours but differentiated in vivo.

REFERENCES

1. Reynolds, B. A. & Weiss, S. Generation of neurons and astrocytes from isolated cells of the adult mammalian central nervous system. *Science* 255, 1707-10 (1992).
2. Garcion, E., Halilagic, A., Faissner, A. & ffrench-Constant, C. Generation of an environmental niche for neural stem cell development by the extracellular matrix molecule tenascin C. *Development* 131, 3423-32 (2004).
3. Morshead, C. M., Benveniste, P., Iscove, N. N. & van der Kooy, D. Hematopoietic competence is a rare property of neural stem cells that may depend on genetic and epigenetic alterations. *Nat Med* 8, 268-73 (2002).
4. Suslov, O. N., Kukekov, V. G., Ignatova, T. N. & Steindler, D. A. Neural stem cell heterogeneity demonstrated by molecular phenotyping of clonal neurospheres. *Proc Natl Acad Sci USA* 99, 14506-11 (2002).
5. Malatesta, P. et al. Neuronal or glial progeny: regional differences in radial glia fate. *Neuron* 37, 751-64 (2003).
6. Anthony, T. E., Klein, C., Fishell, G. & Heintz, N. Radial glia serve as neuronal progenitors in all regions of the central nervous system. *Neuron* 41, 881-90 (2004).
7. Ying, Q.-L., Stavridis, M., Griffiths, D., Li, M. & Smith, A. Conversion of embryonic stem cells to neuroectodermal precursors in adherent monoculture. *Nature Biotechnology* 21, 183-186 (2003).
8. Bain, G., Kitchens, D., Yao, M., Huettner, J. E. & Gottlieb, D. 1. Embryonic stem cells express neuronal properties in vitro. *Dev Biol* 168, 342-57. (1995).
9. Li, M., Pevny, L., Lovell-Badge, R. & Smith, A. Generation of purified neural precursors from embryonic stem cells by lineage selection. *Curr Biol* 8, 971-4 (1998).
10. Aubert, J. et al. Screening for mammalian neural genes via fluorescence-activated cell sorter purification of neural precursors from Sox1-gfp knock-in mice. *Proc Natl Acad Sci USA* 100 Suppl 1, 11836-41 (2003).
11. Stavridis, M. P. & Smith, A. G. Neural differentiation of mouse embryonic stem cells. *Biochem Soc Trans* 31, 45-9. (2003).
12. Campbell, K. & Gotz, M. Radial glia: multi-purpose cells for vertebrate brain development. *Trends Neurosci* 25, 235-8 (2002).
13. Hartfuss, E., Galli, R., Heins, N. & Gotz, M. Characterization of CNS precursor subtypes and radial glia. *Dev Biol* 229, 15-30 (2001).
14. Billon, N., Jolicoeur, C., Ying, Q. L., Smith, A. & Raff, M. Normal timing of oligodendrocyte development from genetically engineered, lineage-selectable mouse ES cells. *J Cell Sci* 115, 3657-65. (2002).
15. Bibel, M. et al. Differentiation of mouse embryonic stem cells into a defined neuronal lineage. *Nat Neurosci* 7, 1003-9 (2004).
16. Gabay, L., Lowell, S., Rubin, L. L. & Anderson, D. J. Deregulation of dorsoventral patterning by FGF confers trilineage differentiation capacity on CNS stem cells in vitro. *Neuron* 40, 485-99 (2003).
17. Hack, M. A., Sugimori, M., Lundberg, C., Nakafuku, M. & Gotz, M. Regionalization and fate specification in neurospheres: the role of Olig2 and Pax6. *Mol Cell Neurosci* 25, 664-78 (2004).
18. Pevny, L. H., Sockanathan, S., Placzek, M. & Lovell-Badge, R. A role for SOX1 in neural determination. *Development* 125, 1967-78. (1998).
19. Heins, N. et al. Emx2 promotes symmetric cell divisions and a multipotential fate in precursors from the cerebral cortex. *Mol Cell Neurosci* 18, 485-502 (2001).
20. Galli, R. et al. Emx2 regulates the proliferation of stem cells of the adult mammalian central nervous system. *Development* 129, 1633-44 (2002).
21. Rakic, P. Elusive radial glial cells: historical and evolutionary perspective. *Glia* 43, 19-32 (2003).
22. Gregg, C. & Weiss, S. Generation of functional radial glial cells by embryonic and adult forebrain neural stem cells. *J Neurosci* 23, 11587-601 (2003).
23. Magrassi, L. et al. Basal ganglia precursors found in aggregates following embryonic transplantation adopt a striatal phenotype in heterotopic locations. *Development* 125, 2847-55 (1998).

24. Brustle, O. et al. In vitro-generated neural precursors participate in mammalian brain development. *Proc Natl Acad Sci USA* 94, 14809-14 (1997).
25. Rossi, F. & Cattaneo, E. Opinion: neural stem cell therapy for neurological diseases: dreams and reality. *Nat Rev Neurosci* 3, 401-9 (2002).
26. Malatesta, P., Hartfuss, E. & Gotz, M. Isolation of radial glial cells by fluorescent-activated cell sorting reveals a neuronal lineage. *Development* 127, 5253-63 (2000).
27. Gottlieb, D. I. Large-scale sources of neural stem cells. *Annu Rev Neurosci* 25, 381-407 (2002).
28. Temple, S. Division and differentiation of isolated CNS blast cells in microculture. *Nature* 340, 471-3 (1989).
29. Johe, K. K., Hazel, T. G., Muller, T., Dugich-Djordjevic, M. M. & McKay, R. D. Single factors direct the differentiation of stem cells from the fetal and adult central nervous system. *Genes Dev* 10, 3129-40 (1996).
30. Frederiksen, K., Jat, P. S., Valtz, N., Levy, D. & McKay, R. Immortalization of precursor cells from the mammalian CNS. *Neuron* 1, 439-48 (1988).
31. Alvarez-Buylla, A., Garcia-Verdugo, J. M. & Tramontin, A. D. A unified hypothesis on the lineage of neural stem cells. *Nat Rev Neurosci* 2, 287-93 (2001).
32. Palmer, T. D., Takahashi, J. & Gage, F. H. The adult hippocampus contains primordial stem cells. *Mol. Cell. Neurosci.* 8, 389-404 (1997).
33. Ying, Q.-L. & Smith, A. G. in *Differentiation of Embryonic Stem Cells* (eds. Wassarman, P. & Keller, G.) 327-341 (Elsevier, 2003).
34. Carbone E and Lux H D (1987) Kinetics and selectivity of a low voltage activated calcium current in chick and rat sensory neurons. J Physiol (Lond) 386:547-570.

PROTOCOL REFERENCES

P1. Ying Q-L, Stavridis M, Griffiths D, Li M, Smith A (2003) Conversion of embryonic stem cells to neuroectodermal precursors in adherent monoculture. Nature Biotechnology 21: 183-186.
P2. Ying Q L, Smith A G (2003) Defined conditions for neural commitment and differentiation. Methods Enzymol 365: 327-341.
P3. Smith A G (1991) Culture and differentiation of embryonic stem cells. J Tiss Cult Meth 13: 89-94.
P4. Stavridis M P, Smith A G (2003) Neural differentiation of mouse embryonic stem cells. Biochem Soc Trans 31: 45-49.
P5. Reynolds B A, Weiss S (1996) Clonal and population analyses demonstrate that an EGF-responsive mammalian embryonic CNS precursor is a stem cell. Dev Biol 175: 1-13.

The invention claimed is:

1. A composition, comprising:
neural stem cells;
EGF; and
FGF-2,
wherein the neural stem cells are in a feeder-free, adherent monolayer culture and wherein at least 95% of said cells are symmetrically-dividing neural stem cells and wherein no more than 1% of the cells are positive for the expression of markers from mature astrocytes, neurons and oligodendrocytes.

2. The composition of claim 1, wherein at least 97% of said neural stem cells are symmetrically-dividing neural stem cells.

3. The composition of claim 1, wherein the neural stem cells are characterized in that they are positive for the expression of RC2, 3CB2, BLBP and Sox-2.

4. The composition of claim 3, wherein the neural stem cells are further characterized in that they are positive for the expression of at least one of (i) GLAST, (ii) Pax-6, (iii) the neural precursor markers nestin or vimentin, (iv) the LewisX antigen, (v) Musashi-1 and (vi) prominin.

5. The composition of claim 4, wherein the neural stem cells are further characterised in that they are negative for the expression of at least one of Oct4 and Nanog.

6. The composition of claim 4, wherein the neural stem cells are positive for the expression of Sox-2, and negative for the expression of Sox-1.

7. A mouse neural stem cell line, wherein said neural stem cells are maintained in the presence of EGF and FGF-2 in a feeder-free, adherent monolayer culture and wherein at least 95% of said cells are symmetrically-dividing neural stem cells and wherein no more than 1% of cells in the line are positive for expression of GFAP or βIII tubulin.

8. A human neural stem cell line, wherein said neural stem cells are maintained in the presence of EGF and FGF-2 in a feeder-free, adherent monolayer culture and wherein at least 95% of said cells are symmetrically-dividing neural stem cells and wherein no more than 1% of cells in the line are positive for expression of markers for mature astrocytes, neurons or oligodendrocytes.

9. A population of neural stem cells, wherein said neural stem cells are maintained in the presence of EGF and FGF-2 in a feeder-free, adherent monolayer culture and wherein at least 95% of said cells are symmetrically-dividing neural stem cells and wherein no more than 1% of the cells are positive for the expression markers for mature astrocytes, neurons, and oligodendrocytes.

10. A cell line, wherein the cells are maintained in the presence of EGF and FGF-2 in a feeder-free, adherent monolayer culture, wherein at least 95% of said cells are symmetrically-dividing neural stem cells and wherein no more than 1% of the cells are positive for the expression of markers for mature astrocytes, neurons, and oligodendrocytes.

11. A composition comprising neural stem cells, EGF, and FGF-2, wherein the neural stem cells are in a feeder-free, adherent monolayer culture and at least 95% of the cells in the composition are symmetrically-dividing neural stem cells and wherein no more than 1% of the cells are positive for the expression of markers for mature astrocytes, neurons, and oligodendrocytes.

12. A composition comprising neural stem cells, EGF, and FGF-2, wherein the neural stem cells are in a feeder-free, adherent monolayer culture, and wherein at least 95% of the cells in the composition are symmetrically-dividing neural stem cells.

* * * * *